US006428998B1

(12) United States Patent
Colige et al.

(10) Patent No.: US 6,428,998 B1
(45) Date of Patent: Aug. 6, 2002

(54) RECOMBINANT N-PROTEINASE AND METHODS AND USES THEREOF

(75) Inventors: Alain Colige, Dave; Charles M. Lapiere, Fraipont, both of (BE); Darwin J. Prockop, Philadelphia, PA (US)

(73) Assignee: University of Liege, Liege (BE)

( * ) Notice: Subject to any disclaimer, the term of this patent is extended or adjusted under 35 U.S.C. 154(b) by 0 days.

(21) Appl. No.: 09/491,522

(22) Filed: Jan. 26, 2000

Related U.S. Application Data

(63) Continuation of application No. 09/237,736, filed on Jan. 26, 1999, now abandoned, which is a continuation of application No. 08/886,333, filed on Jul. 2, 1997, now abandoned.

(60) Provisional application No. 60/021,703, filed on Jul. 3, 1996.

(51) Int. Cl.[7] ............................ C12N 9/64; C12N 5/00; C12N 1/20; C12N 15/00; C07H 21/04

(52) U.S. Cl. .................... 435/226; 435/325; 435/252.3; 435/320.1; 435/348; 435/419; 435/254.2; 536/23.2

(58) Field of Search ...................... 536/23.2; 435/320.1, 435/252.3, 254.2, 419, 325, 226, 348

(56) References Cited

U.S. PATENT DOCUMENTS

| | | | |
|---|---|---|---|
| 4,745,051 A | 5/1988 | Smith et al. | 435/68 |
| 4,946,778 A | 8/1990 | Ladner et al. | 435/69.6 |
| 5,408,040 A | 4/1995 | Grotendorst et al. | 530/399 |

OTHER PUBLICATIONS

Bitter et al., "Expression and Secretion Vectors in Yeast," *Methods in Enzymol. 153*:516–544 (1987).

Brisson et al., "Expression of a Bacterial Gene in Plants by Using a Viral Vector," *Nature 310*:511–514 (1984).

Broglie et al., "Light–Regulated Expression of a Pea Ribulose–1.5–Bisphosphate Carboxylase Small Subunit Gene in Transformed Plant Cells," *Science 224*:838–843 (1984).

Caruthers et al., "New Chemical Methods for Synthesizing Polynucleotides," *Nucleic Acids Res. Symp. Ser. 7*:215–233 (1980).

Chow et al., "Synthesis of Oligodeoxyribonucleotides on Silica Gel Support," *Nucleic Acids Res. 9*:2807–2817 (1981).

Colbere–Garapin et al., "A New Dominant Hybrid Selective Marker For Higher Eukaryotic Cells," *J. Mol. Biol. 150*:1–14 (1981).

Colige et al., "Charaterization and Partial Amino Acid Sequencing of a 107–kDa Procollagen I N–Proteinase Purified by Affinity Chromatography in Immobilized Type XIV Collagen," *J. Biol. Chem. 270*:16724–16730 (1995).

Colige, "cDNA Cloning and Expression of Bovine Procollagen I N–Proteinase: A New Member of the Superfamily of Zinc–Metalloproteinases With Binding Sites for Cells and Other Matrix Components," *Proc. Natl. Acad. Sci. U.S.A. 94*:2374–2379 (1997).

Coruzzi et al., "Tissue–Specific and Light–Regulated Expression of a Pea Nuclear Gene Encoding the Small Subunit of Ribulose–1,5–Bisphosphate Carboxylase," *EMBO Journal 3*:1671–1679 (1984).

Cote et al., "Generation of Human Monoclonal Antibodies Reactive With Cellular Antigens," *Proc. Natl. Acad. Sci. U.S.A. 80*:2026–2030 (1983).

Crea and Horn, "Synthesis of Oligonucleotides on Cellulose by a Phosphotriester Method," *Nucleic Acids Res. 8*:2331–2348 (1980).

Dombrowski and Prockop, "Cleavage of Type I and Type II Procollagens by Type I/II Procollagen N–Proteinase," *J. Biol. Chem. 263*:16545–16552 (1988).

Freije et al., "Molecular Cloning and Expression of Collagenase–3, a Novel Human Matrix Metalloproteinase Produced by Breast Carcinomas," *J. Biol. Chem. 269*(24):16766–16773 (1994).

Gurley et al, "Upstream Sequences Required for Efficient Expression of a Soybean Heat Shock Gene,"*Mol. Cell Biol. 6*:559–565 (1986).

Halila and Peltonen, "Purification of Human Procollagen Type III N–Proteinase From Placenta and Preparation of Antiserum," *Biochem, J. 239*:47–52 (1986).

Halilia et al., "Type III Procollagen N–Proteinase: Isolation of a Candidate cDNA Clone and Assignment of the Corresponding Gene to Human Chromosome 16," *Matrix 13*(1):9–10 (1993).

Hartman and Mulligan, "Two Dominant–Acting Selectable Markers for Gene Transfer Studies in Mammalian Cells," *Proc. Natl. Acad. Sci. U.S.A. 85*:8047–8051 (1988).

Heinemann and Sprague, "Bacterial Conjugative Plasmids Mobilize DNA Transfer Between Bacteria and Yeast," *Nature 340*:205–209 (1989).

Hojima et al., "Type I Procollagen N–Proteinase From Chick Embryo Tendons," *J. Biol. Chem. 264*:11336–11345 (1989).

Hojima et al., "Characterization of Type I Procollagen N–Proteinase From Fetal Bovine Tendon and Skin. Purification of the 500–Kilodalton Form of the Enzyme From Bovine Tendon," *J. Biol. Chem. 269*:11381–11390 (1994).

Huse et al., "Generation of a Large Combinatorial Library of the Immunoglobulin Repertoire in Phage Lambda," *Science 246*:1275–1281 (1989).

(List continued on next page.)

*Primary Examiner*—Rebecca E. Prouty
*Assistant Examiner*—David J Steadman

(57) ABSTRACT

The present invention relates to novel polynucleotide sequences encoding human N-proteinase, and the polypeptides encoded by such polynucleotide sequences. The present invention further relates to methods for using the polynucleotides encoding human N-proteinase to produce the protein.

14 Claims, 10 Drawing Sheets

OTHER PUBLICATIONS

Inouye and Inouye, "Up–Promoter Mutation in the Ipp Gene of *Escherichia coli*," *Nucleic Acids Res. 13*:3101–3110 (1985).

Kadler et al., "Procollagen N–Peptidases: Procollagen N–Proteinases," *Methods Enzymol. 248*:756–771 (1995).

Kohler and Milstein, "Continuous Cultures of Fused Cells Secreting Antibody of Predefined Specificity," *Nature 256*:495–497 (1975).

Kohn et al., "Calf Tendon Procollagen Peptidase: Its Purification and Endopeptidase Mode of Action," *Proc. Natl. Acad. Sci. U.S.A. 71*:40–44 (1974).

Kozbor and Roder, "The Production of Monoclonal Antibodies From Human Lymphocytes," *Immunology Today 4*:72–79 (1983).

Lee and Nathans, "Proliferin Secreted by Cultured Cells Binds to Mannose 6–Phosphate Receptors," *J. Biol. Chem. 263*:3521–3527 (1988).

Logan and Shenk, "Adenovirus Tripartite Leader Sequence Enhances Translation of mRNAs Late After Infection," *Proc. Natl. Acad. Sci. U.S.A. 81*:3655–3659 (1984).

Lowy et al, "Isolation of Transforming DNA: Cloning the Hamster aprt Gene," *Cell 22*:817–823 (1980).

Mackett et al., "Vaccinia Virus: A Selectable Eukaryotic Cloning and Expression Vector," *Proc. Natl. Acad. Sci. U.S.A. 79*:7415–7419 (1982).

Mackett et al., "General Method for Production and Selection of Infectious Vaccinia Virus Recombinants Expressing Foreign Genes," *J. Virol. 49*:857–864 (1984).

Matteucci and Caruthers, "The Synthesis of Oligodeoxypyrimidines on a Polymer Support," *Tetrahedron Letters 21*:719–722 (1980).

Morrison et al., "Chimeric Human Antibody Molecules: Mouse Antigen–Binding Domains with Human Constant Region Domains," *Proc. Natl. Acad. Sci. U.S.A. 81*:6851–6855 (1984).

Mulligan and Berg, "Selection for Animal Cells that Express the *Escherichia coli* Gene Coding for Xanthine–Guanine Phosphoribosyltransferase," 78:2072–2076 (1981).

Neuberger et al., "Recombinant Antibodies Possessing Novel Effector Functions," *Nature 312*:604–608 (1984).

Niemeläet al., "Purification and Characterization of the N–Terminal Propeptide of Human Type III Procollagen," *Biochem.J. 232*:145–150 (1985).

Nusgens and Lapiere, "A Simplified Procedure for Measuring Amino–Procollagen Peptidase Type I," *Anal. Biochem. 95*:406–412 (1979).

Nusgens et al., "Evidence for a Relationship Between Ehlers–Danlose Type VII C in Humans and Bovine Dermatosparaxis," *Nature Genetics 1*:214–217 (1992).

O'Hare et al., "Transformation of Mouse Fibroblasts to Methotrexate Resistance by a Recombinant Plasmid Expressing a Prokaryotic Dihydrofolate Reductase," *Proc. Natl. Acad. Sci. U.S.A. 78*:1527–1531 (1981).

Rose et al., "A Saccharomyces Cerevisiae Genomic Plasmid Bank Based on a Centromere–Containing Shuttle Vector," *Gene 60*:237–243 (1987).

Rosenberg et al., "Vectors for Selective Expression of Cloned DNAs by T7 RNA Polymerase," *Gene 56*:125–135 (1987).

Rüther and Müller–Hill, "Easy Identification of cDNA Clones," *EMBO Journal 2*:1791–1794 (1983).

Santerre et al., "Expression of Prokaryotic Genes for Hygromycin B and G418 Resistance as Dominant–Selection Markers in Mouse L Cells," *Gene 30*:147–156 (1984).

Smith et al., Molecular Engineering of the *Autographa californica* Nuclear Polyhedrosis Virus Genome: Deletion Mutations Within the Polyhedrin Gene, *J. Virol. 46*:584–593 (1983).

Szybalska and Szybalski, "Genetics of Human Cell Lines, IV, DNA–Mediated Heritable Transformation of a Biochemical Trait," *Proc. Natl. Acad. Sci. U.S.A. 48*:2026–2034 (1962).

Takamatsu et al., "Expression of Bacterial Chloramphenicol Actyltransferase Gene in Tobacco Plants Mediated by TMV–RNA," *EMBO Journal 6*:307–311 (1987).

Takeda et al., "Construction of Chimaeric Processed Immunoglobulin Genes Containing Mouse Variable and Human Constant Region Sequences," *Nature 314*:452–454 (1985).

Tanzawa et al., "Type I Procollagen N–Proteinase From Whole Chick Embryos," *J. Biol. Chem. 260*:1120–1126 (1985).

Tuderman and Prockop, "Procollagen N–Proteinase: Properties of the Enzyme Purfied from Chick Embryo Tendons," *Eur. J. Biochem. 125*:545–549 (1982).

Van der Rest and Garrone, "Collagen Family of Proteins," *FASEB J. 5*:2814–2823 (1991).

Van Heeke and Schuster, "Expression of Human Asparagine Synthetase in *Escherichia coli*," *J. Biol. Chem. 264*:5503–5509 (1989).

Wigler et al., "Transfer of Purified Herpes Virus Thymidine Kinase Gene to Cultured Mouse Cells," *Cell 11*:223–232 (1977).

Wigler et al., "Transformation of Mammalian Cells With an Amplifiable Dominant Acting Gene," *Proc. Natl. Acad. Sci. U.S.A. 77*:3567–3570 (1980).

```
GCCCCAGATG TGGGCTGGGC GGCTCGCGGG GAACTTTCGC GCCGGCTGCG AGTGCGGGGC     60
CCCGGCTGCA GTCCGGCTGC CATGGATCCG CCGGCGGGAG CCGCTCGCCG CCTGCTCTGC    120
CCCGCGCTGC TGCTGCTGCT GCTGCTGCTG CCGCCGCCGC TCCTGCCGCC GCCGCCGCCG    180
CCCGCGAACG CCAGGCTCGC CGCCGCCGCC GACCCCCCAG GCGGGCCCCT GGGGCACGGA    240
GCGGAGCGCA TCCTGGCGGT GCCCGTGCGC ACTGACGCCC AGGGCCGCTT GGTGTCCCAC    300
GTGGTGTCGG CAGCTACGTC CAGAGCAGGG GTACGAGCCC GCAGGGCCGC CCCGGTCCGG    360
ACCCCGAGCT TCCCCGGAGG CAACGAGGAG GAGCCTGGCA GTCACCTCTT CTACAATGTC    420
ACGGTCTTTG GCCGAGACCT GCACCTGCGG CTGCGGCCCA ACGCCCGCCT CGTGGCGCCC    480
GGGGCCACTA TGGAGTGGCA GGGCGAGAAG GGCACCACCC GCGTGGAGCC CCTGCTCGGG    540
AGCTGTCTCT ACGTCGGAGA CGTGGCCGGC CTAGCCGAAG CCTCCTCTGT GGCGCTCAGC    600
AACTGCGATG GCTGGCTGG TCTGATCCGG ATGGAGGAGG AGGAGTTCTT CATCGAACCC    660
TTGGAGAAGG GGCTGGCGGC GCAGGAGGCT GAGCAAGGCC GTGTGCATGT GGTGTATCGC    720
CGGCCACCCA CGTCCCCTCC TCTCGGGGGG CCACAGGCCC TGGACACAGG GGCCTCCCTG    780
GACAGCCTGG ACAGCCTCAG CCGCGCCCTG GGCGTCCTAG AGGAGCACGC CAACAGCTCG    840
AGGCGGAGGG CACGCAGGCA TGCTGCAGAC GATGACTACA ACATCGAGGT CCTGCTGGGC    900
GTGGATGACT CTGTGGTGCA GTTCCACGGG AAGGAGCACG TACAGAAGTA CCTGCTGACA    960
CTCATGAACA TTGTCAATGA AATCTACCAT GACGAGTCCT TGGGTGCCCA CATCAACGTG   1020
GTCCTGGTGC GGATCATCCT CCTGAGCTAT GGAAAGTCCA TGAGCCTCAT CGAGATCGGG   1080
AACCCCTCTC AGAGCCTGGA GAATGTCTGC CGCTGGGCCT ACCTCCAGCA GAAGCCAGAC   1140
ACGGGCCACG ATGAATACCA CGATCACGCC ATCTTCCTCA CACGGCAGGA CTTTGGGCCT   1200
TCCGGCATGC AAGGCTATGC TCCTGTCACC GGCATGTGCC ATCCGGTCCG CAGCTGCACC   1260
CTGAACCATG AGGACGGCTT CTCCTCAGCG TTTGTGGTGG CCCATGAGAC TGGCCACGTG   1320
CTGGGCATGG AGCACGACGG GCAGGGCAAC CGCTGTGGCG ACGAGGTGCG GCTGGGCAGC   1380
ATCATGGCGC CCCTGGTGCA GGCCGCCTTC CACCGCTTCC ACTGGTCCCG CTGCAGCCAG   1440
CAGGAGCTGA GCCGCTACCT GCACTCCTAT GACTGCCTGC TGGATGACCC CTTCGCCCAC   1500
GACTGGCCGG CGCTGCCCCA GCTCCCGGGA CTGCACTACT CCATGAACGA GCAATGCCGC   1560
TTTGACTTCG GCCTGGGCTA CATGATGTGC ACGGCGTTCC GGACCTTTGA CCCCTGCAAG   1620
CAGCTGTGGT GCAGCCATCC TGACAACCCC TACTTTTGCA AGACCAAGAA GGGGCCCCCC   1680
TTGGACGGGA CTATGTGTGC ACCTGGCAAG CATTGTTTTA AAGGACACTG CATCTGGCTG   1740
ACACCTGACA TCCTCAAACG GGACGGCAGC TGGGGCGCTT GGAGTCCGTT TGGCTCCTGC   1800
TCACGTACCT GTGGCACGGG CGTGAAGTTC AGGACCCGCC AGTGTGACAA CCCACACCCG   1860
GCCAACGGGG GCCGCACCTG CTCGGGCCTT GCCTACGACT TCCAGCTCTG CAGCCGCCAG   1920
GACTGCCCCG ACTCCCTGGC TGACTTCCGC GAGGAGCAGT GCCGCCAGTG GGACCTGTAC   1980
TTCGAGCACG GCGACGCCCA GCACCACTGG CTGCCCCACG AGCACCGGGA TGCCAAGGAG   2040
AGATGCCACC TGTACTGCGA GTCCAGGGAG ACCGGGGAGG TGGTGTCCAT GAAGCGCATG   2100
GTGCATGATG GGACGCGCTG CTCCTACAAG GACGCCTTCA GCCTCTGTGT GCGCGGGGAC   2160
TGCAGGAAGG TGGGCTGTGA CGGTGTGATC GGCTCCAGCA AGCAGGAAGA CAAGTGTGGC   2220
GTGTGCGGAG GGGACAACAG CCACTGCAAA GTGGTCAAGG GCACGTTCAC ACGGTCACCC   2280
AAGAAGCATG GTTACATCAA GATGTTTGAG ATCCCTGCAG GAGCCAGACA CCTGCTCATT   2340
CAGGAGGTAG ACGCCACCAG CCACCATCTG GCCGTCAAGA ACCTGGAGAC AGGCAAGTTC   2400
ATCTTAAATG AAGAGAATGA CGTGGATGCC AGTTCCAAAA CCTTCATTGC              2450
```

FIG._1A

```
CATGGGCGTG                                                           2460
GAGTGGGAGT ACAGAGACGA GGACGGCCGG GAGACGCTGC AGACCATGGG CCCCCTCCAC   2520
GGCACCATCA CCGTTCTGGT CATCCCGGTG GGAGACACCC GGGTCTCACT GACGTACAAA   2580
TACATGATCC ATGAGGACTC ACTGAATGTC GATGACAACA ACGTCCTGGA AGAGGACTCT   2640
GTGGTCTACG AGTGGGCCCT GAAGAAGTGG TCTCCGTGCT CCAAGCCCTG TGGCGGAGGG   2700
TCCCAGTTCA CCAAGTATGG CTGCCGCCGG AGGCTGGACC ACAAGATGGT ACACCGTGGC   2760
TTCTGTGCCG CCCTCTCGAA GCCCAAAGCC ATCCGCAGAG CGTGCAACCC ACAGGAATGC   2820
TCCCAGCCAG TGTGGGTCAC AGGCGAATGG GAGCCATGTA GCCAGACCTG TGGGCGGACA   2880
GGCATGCAGG TGCGCTCCGT GCGCTGCATT CAGCCGCTAC ACGACAACAC CACCCGCTCC   2940
GTGCACGCCA AGCACTGCAA TGACGCCCGG CCCGAGAGCC GCCGGGCCTG CAGCCGCGAG   3000
CTCTGCCCTG GTCGTTGGCG AGCCGGGCCC TGGTCCCAGT GCTCAGTAAC CTGTGGCAAC   3060
GGCACCCAGG AGCGGCCAGT GCTCTGCCGC ACCGCGGACG ACAGCTTCGG CATCTGCCAG   3120
GAGGAGCGTC CTGAGACAGC GAGGACCTGC AGGCTTGGCC CCTGTCCCCG AAACATCTCA   3180
GATCCCTCCA AGAAGAGCTA CGTAGTTCAG TGGCTGTCCC GCCCGGACCC CGACTCGCCC   3240
ATCCGGAAGA TCTCGTCAAA GGGCCACTGC CAAGGCGACA AGTCAATATT CTGTAGGATG   3300
GAAGTCTTGT CCCGCTATTG CTCCATCCCA GGCTACAACA AGCTGTGCTG CAAGTCCTGT   3360
AACCTGTACA ACAACCTCAC CAACGTGGAG GGCAGGATAG AGCCACCGCC TGGGAAGCAC   3420
AACGACATTG ACGTGTTCAT GCCTACCCTC CCAGTGCCCA CTGTAGCCAT GGAGGTGCGG   3480
CCATCACCAA GCACCCCCCT GGAGGTCCCT CTCAATGCCT CCAGCACCAA TGCCACAGAG   3540
GATCACCCAG AAACCAATGC CGTAGATGAA CCCTACAAAA TCCATGGCCT GGAAGATGAA   3600
GTCCAGCCAC CCAACCTAAT CCCTCGACGA CCGAGCCCCT ATGAAAAGAC CAGAAACCAA   3660
AGAATCCAAG AGCTCATTGA TGAGATGCGG AAGAAAGAGA TGCTCGGAAA GTTCTAATAA   3720
AATGGAAAGA TAGCATCCCT AGCATTTTTT TCTTGCTTAT AGAGATATTC CATGGGATAG   3780
CAAATCCTGT GTCATGGAGA TGAAGTCAAA ATTCCTGATT CCAAAAGGTT TTGAGAAAAC   3840
AAAGAGGGGG AATGACGTAA GAAAGATACG CATGAGCATG TGGTAAGCTA GGTTAGCACG   3900
TGTGCTTCCC AGCCCAGGAG CGACCAAATA CTGTGGTGGC GTCAGGTGTG CACTGGAGAG   3960
GAATATAGAG GCTGTATGGC CTCCCTCACT GAGGGCAGGG CAAGAGGGAT CACTCTACAA   4020
ACAAAAATAG GCCCCAAGTT GCTAAGCAGT GATTGGGAAC CTTCCTTTCC TTGGCGGAGA   4080
TGCATGACAT TCCCTACCGA TCCCCAGACA CAGCCTGTGG GACTCTTAGG AGAAATGGTG   4140
ATTTACTGAA TAACTGACCC GTTGCCGAGA TGAGTACAAT GAAGTGGAGG TGATGAACTC   4200
AAATCGTCTT CCAGGGCCAG GCGGCTGACC GGGGTGAGCG TAGTGGCCCG CTGGGGACCA   4260
TGGCCGCCCT GACAGCCACA CCCACCTGGA GCTGACTTGG TTCTGGCTGT TGCTGCCACT   4320
GTGAAATCTG TATCTCTCTC CATCTCTGCT CTACTATCCC CGGCCTTGCC AGACAGTGTT   4380
CTTTTTCGGA AGAAGTCTAG ATTTTTGCAT GAAAAAAACT CAATCTTTAA AGGTCGACTC   4440
AGAACATTTT AAGGAGGCCT CCACTTGGTC TGATGCAGTC TTGCTAATTA AGAACTAAAA   4500
GGCTTCTGAC CTTCTTGGTG CTCATGCTGT ACGGCATCTG AATGTCTCGA CCGAGTCTGA   4560
GCCGTGCAGC TGTCCTCCAC CTGCGAAAGT AATGAGAATC CTATCACGGG ACATAAGGAT   4620
AGGTCTAAAC AGGGTCCATG CCAAGAAAAC AGTGGGGTGC TCTCCCAGGC CTCTCCCCTG   4680
TCCACTAACC CTGGCCTTGC CGGCTGCCTT CCAGGCTCTG GGGGAAGAGC TCCTGCATTC   4740
TTCCCTGGCC ACCTTGGCTC CAGGGCTCCC CAAGAGCCTC TTCCCTCCCC AAGTACCTGA   4800
GAAAGATGAG AGAGGCACGT GCTCTGCTGG GAAGGTCCAG TGAGCGGTTC AAGGGCCTGG   4860
AATCTCCCTA CGGCCAAGTC TAAGGGTTCT GGGATTCTGG                         4900
```

FIG._1B

```
GCTTTGTGGG CTTTGCTTGC                                             4920
TTGCTGCGAA TGGGCTTTCC CTGTCCCGCC TGCCCCACTT GCTTTGTTTT CAGAAGCTCC 4980
AGAACCCAGC AGTGACTGCA AAATGTGGCT TGATGGGGGC TTAGGGTGGG AGATGGGGAG 5040
AGCTACATTG TCTTTTGCTC CTTGAAAACT TTAATAGCTC CTATTTTCCA GAGAATGGTG 5100
CTTTGTGAGC AACATGCGAG TAAGAGAGAA ATAGGAGGAA GGGGGAGTAG GGGCGGATGG 5160
GAGAAGAGTG GCTCATTTTT ACCTCTCACT GCCTGACATT TTGTGAACGT GAAGCTTAAA 5220
CTTTCTGGGC TTACAAGACC CAGGGGCACG TCAGCTCCTT AGATGGGCTC AGCCTGACAC 5280
ATAATTCTTA AACCTTTCCT GTTTAAGAAA CTTCTAGAGG CTGTGTACTC TCACCAATCC 5340
TCTTCGAGAA TTTGTTCATG TGTATTTCCC CATTATATGG ATGAGGCTCA GGATAACAGC 5400
ATAGTGGCTA CCTTCTACTG AGTTTTGAGG TGCTAATAAG TATGTTTGTC TGAGGCTGCA 5460
CATGTGGGTG GCTCTGTGTG TATGATCCAA GGGACAAAAT GACGATGTAG AACCAGCAAG 5520
AACGGAATCT GGCCTGATGC TTCAGTCTCC ACCTGGGTGA TGGTAGCCTC CCGCCCTCCA 5580
CCACCGCATC CCACACGTGC TGCGCACTGT CCCCGTGTCT CCTGGAGAAC CAAACTGGAG 5640
AAAACCTTTC TGAGTATCTC TCATAGTACC CCTTCCTTAA GAAGATGTGG TTTAGAGCAT 5700
GTGTGCAATC CTGCCTCTGT AATTAGGAAA CGGAGCCCGA GGCTTTCCAT TGTTGGTTGA 5760
ACCCAGGACA GCTGGTGCTA TTCACAGGCT GAAGAACTGG GCACTTCTTA CTTGGGTCTG 5820
TCCTAGGATG TGGAGGAAGT TCAGGACTAA CGCTAGGCAG AGAGTATGAC TCGGTTTACC 5880
CAGCCTAGGG GCCTCTGGAT GGGAACACTC CATTCCAAGA TCTCAGCAGA GCAGGGCTTC 5940
CTGGCTTGAG GCTGGAAGCC TTTGGGAAGA GGCCCAGCTG GGACATTACC TGGCACCTTC 6000
TTCCCGTTGA AGGGAGCAAG GTGCCCTCTG GGATGACAGC CAGACCCTTG TGCCATCCTC 6060
AATCTTGAGC CATATATCAA GAGTCCTCTA GAGCCGGATG GTCCTCAAAA GTCTGTCCAA 6120
GGAATGCCAA CGTTCACCGG GCTTGAGAAA CGACGCAAAT CTCTGAGCTG GGGACCACTT 6180
GGAGAACCGG CTTAGTAACA GTCCTGATCT TCGCAAGCCA GTTGTTGTGC ATCTGAGGGG 6240
CTCCTGGCGC CCAGAGGAGG CAGACAGATG CTTCTAGCTG AGTTTCTAAC CGCATGATGA 6300
GACTCAGACC TTCCGCTGCA TAGAAAATTG CAACAGTGTC CGGAGTCATT TTTCCTTAGT 6360
GGGCAGACTC GTGTTAGATT TGGGAACCCA GCTCTTGATT ACTCCTTTTG GAAAACCCAT 6420
GGAATTTCAT GTATAAGGCT TTCATTTGTA TTTTAAGGTT TTTTGTTTGT TTGAGTATAA 6480
CATGGTGCTC AATAGCAACA TCTTAGCAGA TGAAGCAGTT TATGATTCCA CTCCCTCCTG 6540
TATGACAGGT AGCCACTATA CTGAATCAAG GTGCTGAACT CAAATCACAA AATTCTGGCT 6600
TACCGATACA ACAACCAATA CATCTTTGTT TGTAATAAAA AATTTGACTC CTTACTTTTA 6660
TAACTTATTA AAGTTAAAAT GTCTGTGTTT TT                               6692
```

*FIG._1C*

MDPPAGAARR LLCPALLLLL LLLPPPLLPP PPPPANARLA AAADPPGGPL GHGAERILAV
PVRTDAQGRL VSHVVSAATS RAGVRARRAA PVRTPSFPGG NEEEPGSHLF YNVTVFGRDL
HLRLRPNARL VAPGATMEWQ GEKGTTRVEP LLGSCLYVGD VAGLAEASSV ALSNCDGLAG
LIRMEEEEFF IEPLEKGLAA QEAEQGRVHV VYRRPPTSPP LGGPQALDTG ASLDSLDSLS
RALGVLEEHA NSSRRRARRH AADDDYNIEV LLGVDDSVVQ FHGKEHVQKY LLTLMNIVNE
IYHDESLGAH INVVLVRIIL LSYGKSMSLI EIGNPSQSLE NVCRWAYLQQ KPDTGHDEYH
DHAIFLTRQD FGPSGMQGYA PVTGMCHPVR SCTLNHEDGF SSAFVVAHET GHVLGMEHDG
QGNRCGDEVR LGSIMAPLVQ AAFHRFHWSR CSQQELSRYL HSYDCLLDDP FAHDWPALPQ
LPGLHYSMNE QCRFDFGLGY MMCTAFRTFD PCKQLWCSHP DNPYFCKTKK GPPLDGTMCA
PGKHCFKGHC IWLTPDILKR DGSWGAWSPF GSCSRTCGTG VKFRTRQCDN PHPANGGRTC
SGLAYDFQLC SRQDCPDSLA DFREEQCRQW DLYFEHGDAQ HHWLPHEHRD AKERCHLYCE
SRETGEVVSM KRMVHDGTRC SYKDAFSLCV RGDCRKVGCD GVIGSSKQED KCGVCGGDNS
HCKVVKGTFT RSPKKHGYIK MFEIPAGARH LLIQEVDATS HHLAVKNLET GKFILNEEND
VDASSKTFIA MGVEWEYRDE DGRETLQTMG PLHGTITVLV IPVGDTRVSL TYKYMIHEDS
LNVDDNNVLE EDSVVYEWAL KKWSPCSKPC GGGSQFTKYG CRRRLDHKMV HRGFCAALSK
PKAIRRACNP QECSQPVWVT GEWEPCSQTC GRTGMQVRSV RCIQPLHDNT TRSVHAKHCN
DARPESRRAC SRELCPGRWR AGPWSQCSVT CGNGTQERPV LCRTADDSFG ICQEERPETA
RTCRLGPCPR NISDPSKKSY VVQWLSRPDP DSPIRKISSK GHCQGDKSIF CRMEVLSRYC
SIPGYNKLCC KSCNLYNNLT NVEGRIEPPP GKHNDIDVFM PTLPVPTVAM EVRPSPSTPL
EVPLNASSTN ATEDHPETNA VDEPYKIHGL EDEVQPPNLI PRRPSPYEKT RNQRIQELID
EMRKKEMLGK F

FIG._1D

MDPPAGAARR LLCPALLLLL LLLPPPLLPP PPPPANARLA AAADPPGGPL
GHGAERILAV PVRTDAQGRL VSHVVSAATS RAGVRARRAA PVRTPSFPGG
NEEEPGSHLF YNVTVFGRDL HLRLRPNARL VAPGATMEWQ GEKGTTRVEP
LLGSCLYVGD VAGLAEASSV ALSNCDGLAG LIRMEEEEFF IEPLEKGLAA
QEAEQGRVHV VYRRPPTSPP LGGPQALDTG ASLDSLDSLS RALGVLEEHA
NSSRRRARRH AADDDYNIEV LLGVDDSVVQ FHGKEHVQKY LLTLMNIVNE
IYHDESLGAH INVVLVRIIL LSYGKSMSLI EIGNPSQSLE NVCRWAYLQQ
KPDTGHDEYH DHAIFLTRQD FGPSGMQGYA PVTGMCHPVR SCTLNHEDGF
SSAFVVAHET GHVLGMEHDG QGNRCGDEVR LGSIMAPLVQ AAFHRFHWSR
CSQQELSRYL HSYDCLLDDP FAHDWPALPQ LPGLHYSMNE QCRFDFGLGY
MMCTAFRTFD PCKQLWCSHP DNPYFCKTKK GPPLDGTMCA PGKFRPGAVA
HACYPSTLGG QGRWIA

FIG._2B

```
GCCCCAGATG TGGGCTGGGC GGCTCGCGGG GAACTTTCGC GCCGGCTGCG AGTGCGGGGC     60
CCCGGCTGCA GTCCGGCTGC CATGGATCCG CCGGCGGGAG CCGCTCGCCG CCTGCTCTGC    120
CCCGCGCTGC TGCTGCTGCT GCTGCTGCTG CCGCCGCCGC TCCTGCCGCC GCCGCCGCCG    180
CCCGCGAACG CCAGGCTCGC CGCCGCCGCC GACCCCCCAG GCGGGCCCCT GGGGCACGGA    240
GCGGAGCGCA TCCTGGCGGT GCCCGTGCGC ACTGACGCCC AGGGCCGCTT GGTGTCCCAC    300
GTGGTGTCGG CAGCTACGTC CAGAGCAGGG GTACGAGCCC GCAGGGCCGC CCCGGTCCGG    360
ACCCCGAGCT TCCCCGGAGG CAACGAGGAG GAGCCTGGCA GTCACCTCTT CTACAATGTC    420
ACGGTCTTTG GCCGAGACCT GCACCTGCGG CTGCGGCCCA ACGCCCGCCT CGTGGCGCCC    480
GGGGCCACTA TGGAGTGGCA GGGCGAGAAG GGCACCACCC GCGTGGAGCC CCTGCTCGGG    540
AGCTGTCTCT ACGTCGGAGA CGTGGCCGGC CTAGCCGAAG CCTCCTCTGT GGCGCTCAGC    600
AACTGCGATG GGCTGGCTGG TCTGATCCGG ATGGAGGAGG AGGAGTTCTT CATCGAACCC    660
TTGGAGAAGG GGCTGGCGGC GCAGGAGGCT GAGCAAGGCC GTGTGCATGT GGTGTATCGC    720
CGGCCACCCA CGTCCCCTCC TCTCGGGGGG CCACAGGCCC TGGACACAGG GGCCTCCCTG    780
GACAGCCTGG ACAGCCTCAG CCGCGCCCTG GGCGTCCTAG AGGAGCACGC CAACAGCTCG    840
AGGCGGAGGG CACGCAGGCA TGCTGCAGAC GATGACTACA ACATCGAGGT CCTGCTGGGC    900
GTGGATGACT CTGTGGTGCA GTTCCACGGG AAGGAGCACG TACAGAAGTA CCTGCTGACA    960
CTCATGAACA TTGTCAATGA AATCTACCAT GACGAGTCCT TGGGTGCCCA CATCAACGTG   1020
GTCCTGGTGC GGATCATCCT CCTGAGCTAT GGAAAGTCCA TGAGCCTCAT CGAGATCGGG   1080
AACCCCTCTC AGAGCCTGGA GAATGTCTGC CGCTGGGCCT ACCTCCAGCA GAAGCCAGAC   1140
ACGGGCCACG ATGAATACCA CGATCACGCC ATCTTCCTCA CACGGCAGGA CTTTGGGCCT   1200
TCCGGCATGC AAGGCTATGC TCCTGTCACC GGCATGTGCC ATCCGGTCCG CAGCTGCACC   1260
CTGAACCATG AGGACGGCTT CTCCTCAGCG TTTGTGGTGG CCCATGAGAC TGGCCACGTG   1320
CTGGGCATGG AGCACGACGG GCAGGGCAAC CGCTGTGGCG ACGAGGTGCG GCTGGGCAGC   1380
ATCATGGCGC CCCTGGTGCA GGCCGCCTTC CACCGCTTCC ACTGGTCCCG CTGCAGCCAG   1440
CAGGAGCTGA GCCGCTACCT GCACTCCTAT GACTGCCTGC TGGATGACCC CTTCGCCCAC   1500
GACTGGCCGG CGCTGCCCCA GCTCCCGGGA CTGCACTACT CCATGAACGA GCAATGCCGC   1560
TTTGACTTCG GCCTGGGCTA CATGATGTGC ACGGCGTTCC GGACCTTTGA CCCCTGCAAG   1620
CAGCTGTGGT GCAGCCATCC TGACAACCCC TACTTTTGCA AGACCAAGAA GGGGCCCCCC   1680
TTGGACGGGA CTATGTGTGC ACCTGGCAAG TTCAGGCCGG GCGCGGTGGC TCATGCCTGT   1740
TATCCCAGCA CTTTGGGAGG CCAAGGTAGG TGGATCGCCT GAGGTCAGAA GTTCAAGACA   1800
AGTGTGGTTA ACATGGCAAA ATCCCGTCTC TACTAAAAAT ACAAAAATTA GCTGGGCGCG   1860
GTGGTGGGTG CCTGTAATCC CAGCTACTCC GGAGGCTGAG GCATGAAAAT CGTTTGAGCC   1920
CAGGAGGCGG AGGTTGCGGT GAGCCAAGAT CGCGTCGCTG CTTCCAGTCT GGATCACACA   1980
GCAAGACCCT GTCTCAAAAA ATAAAAATAA AAGTGAAGTG CAC                     2023
```

FIG._2A

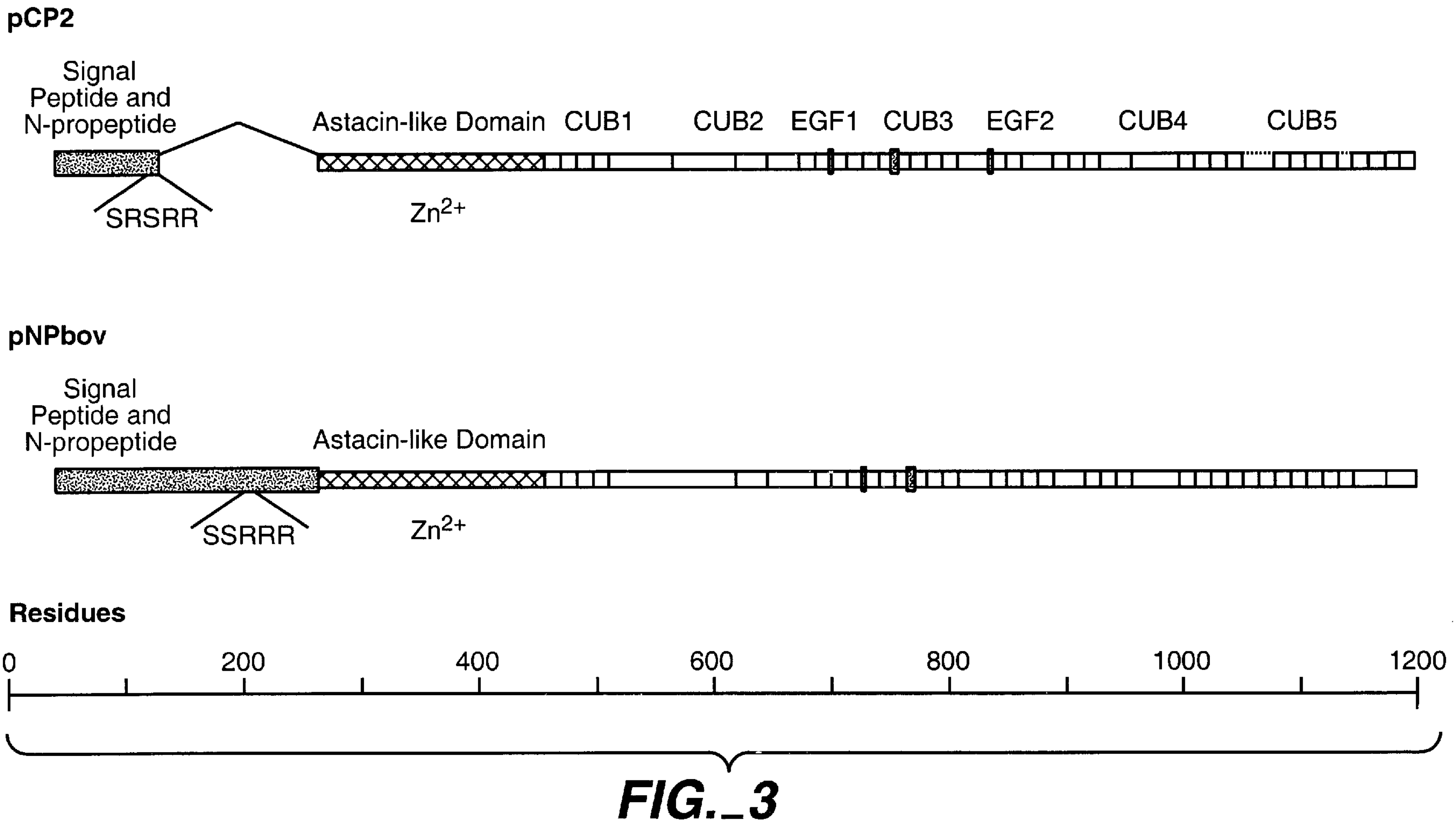
FIG._3

```
TCGAGCCCTC CTCCGCCCCG CGCCCTGCGG TGCTGCAGCT GCGGGCGGCT CCAGCTGCCC   60
CAGATGTGGG CTGGGCGGCG CGCGGGGAAC TTTCGCGCCG GCTGCGAGTG CGGGGCCCCG  120
GCTGTGGTCC GGCTGCCATG GATCCGCCGG CGGGAGCCGC CGGCCGCCTG CTCTGCCCCG  180
CGCTGTTGCT GCTCCTGCTG CTGCCGCTGC CCGCGGACGC CCGGCTCGCC GCCGCTGCCG  240
CCGACCCCCC AGGCGGGCCC CAGGGGCACG GAGCCGAGCG CATCCTGGCG GTGCCGGTGC  300
GCACTGACGC CCAGGGCCGC TTGGTGTCCC ACGTGGTGTC GGCGGCGACG GCCCCAGCTG  360
GGGTGCGGAC CCGCAGGGCC GCCCCTGCCC AGATCCCGGG GCTCTCTGGA GGCAGCGAGG  420
AGGACCCCGG TGGCCGCCTC TTCTACAATG TTACGGTGTT TGGCCGAGAC CTGCACCTGC  480
GGCTGCGGCC CAACGCCCGC CTCGTGGCGC CTGGGGCCAC GGTGGAGTGG CAGGGAGAAT  540
CGGGTGCCAC CCGCGTGGAG CCCCTGCTTG GGACCTGCCT CTACGTCGGA GACGTCGCGG  600
GCCTGGCTGA ATCCTCTTCC GTGGCGCTCA GCAACTGCGA TGGGCTGGCT GGCCTGATCC  660
GTATGGAAGA GGAGGAATTC TTTATTGAGC CCCTGGAGAA AGGTCTGGCG GCGAAGGAGG  720
CCGAACAGGG CCGTGTACAC GTGGTGTATC ATCGACCGAC CACCTCCAGA CCCCCTCCTC  780
TGGGGGGGCC ACAGGCCCTG GACACAGGGA TCTCCGCAGA CAGCCTGGAC AGCCTCAGCC  840
GTGCTCTGGG TGTTCTGGAG GAGCGAGTCA ACAGCTCCAG GCGGAGGATG CGCAGGCATG  900
CTGCCGACGA CGACTACAAC ATCGAGGTCC TGCTTGGGGT GGACGACTCT GTGGTCCAGT  960
TCCACGGGAC GGAGCACGTG CAGAAGTACC TGCTCACCCT CATGAACATT GTCAACGAAA 1020
TCTATCACGA TGAGTCCTTG GGGGCCCACA TCAATGTCGT CCTGGTGCGG ATAATCCTGC 1080
TGAGCTACGG GAAGTCCATG AGTCTCATTG AGATTGGGAA CCCCTCTCAA AGTCTGGAGA 1140
ATGTTTGCCG CTGGGCCTAC CTCCAGCAGA AGCCAGACAC TGATCACGAC GAGTACCACG 1200
ATCACGCCAT ATTCCTCACA CGGCAGGACT TCGGGCCCTC GGGCATGCAA GGCTATGCTC 1260
CTGTCACTGG GATGTGCCAC CCCGTCCGCA GCTGCACGCT GAACCACGAG GACGGCTTCT 1320
CCTCTGCGTT CGTGGTGGCC CACGAGACTG GCCATGTGCT GGGCATGGAG CATGATGGGC 1380
AGGGCAACCG CTGCGGTGAC GAGGTGCGGC TGGGCAGCAT CATGGCGCCC CTGGTGCAGG 1440
CAGCCTTCCA TCGCTTCCAC TGGTCCCGCT GCAGCCAGCA GGAGCTGAGC CGCTACCTGC 1500
ACTCCTATGA CTGCCTGCGG GATGACCCCT TCACCCACGA CTGGCCGGCG CTGCCCCAGC 1560
TCCCCGGGCT GCACTACTCC ATGAACGAGC AGTGCCGTTT CGACTTTGGC CTTGGTTACA 1620
TGATGTGTAC CGCGTTCCGG ACCTTCGACC CGTGCAAACA GCTGTGGTGC AGCCACCCTG 1680
ACAACCCCTA CTTTTGCAAG ACAAAGAAGG GGCCACCCCT GGATGGGACC ATGTGTGCGC 1740
CTGGCAAGCA CTGCTTTAAA GGACACTGCA TCTGGCTGAC ACCTGACATT CTCAAACGAG 1800
ATGGCAACTG GGGTGCCTGG AGTCCCTTCG GCTCCTGCTC GCGTACCTGC GGCACAGGTG 1860
TGAAGTTCAG GACCCGTCAG TGCGACAACC CACACCCAGC CAATGGGGGC CGCACATGCT 1920
CGGGCCTCGC CTACGATTTC CAGCTCTGCA ACTCGCAGGA CTGCCCTGAC GCGCTGGCCG 1980
ACTTCCGCGA GGAGCAGTGC CGGCAGTGGG ACCTGTACTT CGAGCATGGT GACGCTCAAC 2040
ACCACTGGCT GCCCCACGAG CACCGGGACG CCAAGGAGCG GTGTCATCTC TACTGTGAGT 2100
CCAAGGAGAC CGGGGAGGTG GTGTCCATGA AGCGTATGGT GCATGACGGG ACACGCTGTT 2160
CCTACAAGGA CGCCTTCAGC CTCTGCGTGC GTGGGGACTG CAGGAAGGTG GGCTGTGACG 2220
GGGTGATCGG CTCCAGCAAG CAGGAGGACA AGTGTGGTGT GTGCGGAGGG GACAACTCCC 2280
ACTGCAAGGT GGTCAAGGGC ACGTTCTCGC GCTCGCCCAA GAAGCTTGGT TACATCAAGA 2340
TGTTTGAGAT CCCGGCAGGA GCCAGACACC TGCTAATCCA GGAAGCAGAC ACCACCAGCC 2400
ATCACCTGGC CGTCAAAAAC CTGGAGACAG GCAAGTTCAT TTTAAATGAG            2450
```

FIG._4A

GAGAATGACG 2460
TGGATCCCAA CTCCAAGACC TTCATCGCCA TGGGCGTGGA GTGGGAGTAC CGGGATGAGG 2520
ACGGCCGGGA GACGCTGCAG ACCATGGGCC CCCTCCACGG CACCATCACT GTGCTGGTCA 2580
TCCCAGAGGG GGACGCCCGC ATCTCACTGA CCTACAAGTA CATGATCCAT GAGGACTCGC 2640
TCAATGTGGA TGACAACAAC GTCCTGGAAG ACGACTCTGT GGGCTATGAG TGGGCCCTGA 2700
AGAAGTGGTC GCCCTGCTCC AAGCCCTGCG GTGGAGGGTC CCAATTCACC AAGTATGGCT 2760
GCCGCCGGAG GCTGGACCAC AAGATGGTGC ACCGAGGCTT CTGCGACTCC GTCTCAAAGC 2820
CCAAAGCCAT CCGCCGGACC TGCAACCCAC AGGAGTGCTC CCAGCCCGTG TGGGTCACGG 2880
GTGAGTGGGA GCCGTGCAGC CGGAGCTGTG GGCGGACAGG CATGCAGGTT CGCTCTGTGC 2940
GCTGTGTTCA GCCTCTGCAC AACAACACCA CCCGCTCCGT GCACACCAAG CACTGCAATG 3000
ACGCTCGACC CGAGGGCCGC CGGGCCTGCA ACCGCGAGCT GTGCCCTGGC CGGTGGCGGG 3060
CTGGATCCTG GTCCCAGTGC TCAGTAACCT GTGGAAACGG CACCCAGGAA CGGCCAGTGC 3120
TCTGCCGAAC TGCGGACGAC AGTTTCGGGG TGTGCCGGGA GGAGCGGCCT GAGACGGCAA 3180
GGATCTGCAG GCTTGGCCCC TGTCCCCGAA ACACCTCTGA CCCCTCCAAG AAGAGCTACG 3240
TGGTCCAGTG GCTATCCCGA CCGGACCCCA ACTCGCCAGT CCAGGAGACC TCGTCAAAGG 3300
GCCGCTGCCA AGGTGACAAG TCAGTGTTCT GTAGGATGGA AGTCTTGTCT CGTTATTGCT 3360
CCATCCCAGG CTACAATAAG CTGTGCTGCA AGTCCTGTAA CCCGCACGAC AACCTCACTG 3420
ATGTGGACGA CAGGGCAGAG CCACCCTCTG GGAAGCACAA TGACATTGAA GAGCTCATGC 3480
CCACCCTTTC AGTGCCCACT CTAGTCATGG AGGTGCAGCC TCCGCCAGGC ATACCCCTGG 3540
AGGTGCCTCT CAATACTTCC AGCACCAATG CCACCGAGGA CCATCCAGAA ACCAATGCTG 3600
TGGATGTGCC CTACAAAATC CCTGGCCTGG AAGATGAAGT CCAGCCACCC AACCTGATCC 3660
CTCGACGACC GAGCCCATAT GAAAAGACCA GAAACCAAAG AATCCAAGAG CTCATTGATG 3720
AGATGAGGAA GAAAGAGATG CTCGGAAAGT TCTAATAAAA TGGAAAGATA GCATCAATAG 3780
CTTTTTTTTG CTTGCTTATA GAGATATTCC ATGGCAACTC CTGTGTTGTG GAGATGAAGT 3840
CAGATTCCTG ACTCCAAAAG GTTTTGAGGA AACAAAGAAG GAGAATAATG TAAATATATA 3900
GCTATATTTA CATTATACAC ACACACACAC ACACACATAG TTGTAAGCAT GTGGCAACTA 3960
GGTTGGTACC TATGTTTCCT AGTCCTGGAA TGTTCTAAGT CCTGCACTGG GGTTGGGTGT 4020
GGGGTAGAGA GGAATATGGA GGCTCTACAC CTCCCATCAA TGAGGGACAG CAGGAGGGAG 4080
AGAAAAAACC TTTGCCCCAA GTTTCTGAGC AGTGATTGCG AATCTTTTCC TTGCGGTGAC 4140
AACCCTGCTG GAGACGCAGG ACAGTTCCTA CCAATCTCCA GGTTGAGGTA CAAGACCCAT 4200
GGGGCTCTTA CAAGAAACAG TGATTTATTT ACTAAGTGAC CAGTCATTAA GACGAATGCA 4260
GTGAAGTGGA GGTCATGAAT TCCAGCAAAC TCCAGGACGA GGTGGTGAGG CAGGTGGCGT 4320
GGATGAGTGT GGTCACCAGC TGGCACTCCC AGGCTCTCAC ACCTCTCTCT TCTTCACTAA 4380
CCTTGGCCTT GCTTGTCACC TCTGGCCAGC CTGGCCTCAG GCCTGGGGCT CCCCAGAGAC 4440
ACTCTCTGCT TCCTCAAGTC ACTGGAAGGA TGAAGGAGGC ATGCACTCTG CTGGAAAATC 4500
CAGTGAGTGG TCAGGGCTCA TTTTTCTGTG TGTGAACATG TAGCTTAAAC TTCCCGAAAT 4560
TACAGGACCC AAACACCAAG 4580

FIG._4B

MDPPAGAAGRLLCPALLLLLLLPLPADARLAAAAADPPGGPQGHGAERILAVPVRTDAQGRLVSHVVSAATAPAGVRTRRAAPAQI

PGLSGGSEEDPGGRLFYNVTVFGRDLHLRLRPNARLVAPGATVEWQGESGATRVEFLLGTCLYVGDVAGLAESSSVALSNCDGLAG

LIRMEEEEFFIEPLEKGLAAKEAEQGRVHVVYHRFTTSRPPPLGGPQALDTGISADSLDSLSRALGVLEERVNSSRRRMRRHAADDD

YNIEVLLGVDDSVVQFHGTEHVQKYLLTLMNIVNEIYHDESLGAHINVVLVRIILLSYGKSMSLIEIGNPSQSLENVCRWAYLQQKPDT

DHDEYHDHAIFLTRQDFGPSGMQGYAPVTGMCHPVRSCTLNHEDGFSSAFVVAHETGHVLGMEHDGQGNRCGDEVRLGSIMAP

*Zn++ binding site* *Met-turn*

LVQAAFHRFHWSRCSQQELSRYLHSYDCLRDDFFTHDWPALPQLPGLHYSMNEQCRFDFGLGYMMCTAFRTFDPCKQLWCSHPDN

PYFCKTKKGPPLDGTMCAPGKHCFKGHCTWLTFDILKRDGNWGAWSPFGSCSRTCGTGVKFRTRQCDNPHPANGGRTCSGLAYD

*properdin repeat 1*

FQLCNSQDCPDALADFREEQCRQWDLYFEHGDAQHHWLPHEHRDAKERCHLYCESKETGEVVSMKRMVHDGTRCSYKDAFSLCV

RGDCRKVGCDGVIGSSKQEDKCGVCGGDNSHCKVVKGTFSRSPKKLGYIKMFEIPAGARHLLIQEADTTSHHLAVKNLETGKFILNE

ENDVDPNSKTFIAMGVEWEYRDEDGRETLQTMGPLHGTTTVLVIPEGDARISLTYKYMIHEDSLNVDDNNVLEDDSVGYEWALKK

*properdin*

WSPCSKPCGGGSQFTKYGCRRRLDHKMVHRGFCDSVSKPKAIRRTCNPQECSQPVWVTGEWEPCSRSCGRTGMQVRSVRCV

*repeat 2* *properdin repeat 3*

QPLHNNTTRSVHTKHCNDARPEGRRACNRELCPGRWRAGSWSQQCSVTCGNGTQERPVLCRTADDSFGVCREERPETARICRLGP

*properdin repeat 4*

CPRNTSDPSKKSYVVQWLSRPDPNSPVQETSSKGRCQGDKSVFCRMEVLSRYCSIPGYNKLCCKSCNPHDNLTDVDDRAEPPSGKH

NDIEELMPTLSVPTLVMEVQPPPGIPLEVPLNTSSTNATEDHPETNAVDVPYKIPGLEDEVQPPNLIPRRPSPYEKTRNQRIQELIDEMR

KKEMLGKF

FIG._5

```
                d   f         v
M   I   H   E   y   q   L   N   f   D   D   N
                p   v

3' TAC TAG GTA CTC IGA IAC GACTTG AAA CTA CTG TT 5'OP10
                    TG  TG        C C

                              3'TTA AAI CTA CTA TTA5'OP10
```

---

```
F I L N E  E N D  V D P N S K

   3'TTA CTC CTC TTA CTA CAI CTA G'  5'       OP1
       G   T   T   G   G       G

                 3'CTA GGA TTA ACI TTC  5'    OP8
                     G   C   G TG   T
                         G
                         T
```

FIG._6

RECOMBINANT N-PROTEINASE AND METHODS AND USES THEREOF

This application is a continuation of U.S. application Ser. No. 09/237,736, filed Jan. 26, 1999, now abandoned, which is a continuation of U.S. application Ser. No. 08/886,333, filed July 2, 1997, now abandoned, and claims benefit of U.S. Provisional Application Serial No. 60/021,203, filed Jul. 3, 1996.

The information disclosed in this Specification was made in part with Government grant support, awarded by the National Institute of Health. The government may have certain rights in the invention disclosed in this Specification.

I. FIELD OF THE INVENTION

This invention relates generally to the field of N-proteinase and the production, uses and methods thereof.

II. BACKGROUND OF THE INVENTION

The ExtraCellular Matrix. The most abundant component of the extracellular matrix is collagen. Collagen molecules are generally the result of the trimeric assembly of three polypeptide chains containing, in their primary sequence, $(\text{-Gly-X-Y-})_n$ repeats which allow for the formation of triple helical domains. Van der Rest et al. 1991, *FASEB J.* 5:2814–2823.

During their biosynthesis, the fibrillar collagens, including collagen types I, II and III, are synthesized as precursors, known as procollagens. These procollagens are comprised of a central triple-helical collagen domain extended by propeptides both at the molecules' carboxyl and amino ends. These propeptides, designated as C-propeptide (for the propeptide found at the carboxyl terminal end of procollagen) and N-propeptide (for the propeptide found at the amino terminal end of procollagen), are cleaved during post-translational events by the enzymes C-proteinase and N-proteinase, respectively.

Diseases Associated with the Abnormal Production of Collagen. An array of critical diseases has been associated with the inappropriate or unregulated production of collagen, including pathological fibrosis or scarring, including endocardial sclerosis, idiopathic interstitial fibrosis, interstitial pulmonary fibrosis, perimuscular fibrosis, Symmers' fibrosis, pericentral fibrosis, hepatitis, dermatofibroma, binary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture, payronles disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. One strategy for the treatment of these diseases is the inhibition of the pathological overproduction of collagen. The identification and isolation of enzymes involved in the collagen production and processing are therefore of major medical interest to provide for suitable targets for drug development.

Similarly, a strategy for the treatment of diseases resulting from the pathological underproduction of collagen, where the underproduction of collagen is the consequence of improper processing of procollagen, is the administration of C-proteinase.

N-Proteinase. N-proteinase is the post-translational enzyme responsible for cleaving the N-propeptide from the procollagen molecule. Type III N-proteinase is specific to type III procollagen and excises the N-propeptide from type III procollagen only. In contrast, type I N-proteinase acts on both collagen types I and II.

The purification of both type I and type III N-proteinase from natural sources, including chicken embryos, has been previously reported. For example, with respect to type III N-proteinase, the isolation and purification of human enzyme from ascitic fluid and placenta were reported in 1985 and 1986, respectively. See, Niemela et al., 1985, *Biochem. J.* 232:145–150; Halila and Peltonen, 1986, *Biochem. J.* 239:47–52. The isolation and at least partial purification of type I N-proteinase from chick and bovine sources, have also been reported previously. See, Kohn et al., 1974, *Proc. Natl. Acad. Sci. USA* 71:44; Tuderman and Prockop, 1982, *Eur. J. Biochem.* 125:545–549; Tazawa et al., 1985, *J. Biol. Chem.* 260:1120–1126; Hojima et al., 1994, *J. Biol. Chem.* 269:11381–11390; Colige et al., 1995, *J. Biol. Chem.* 270:16724–16730.

The kinetics of purified naturally-occurring N-proteinases, both Types I and III, have also been studied. Dombrowski and Prockop, 1988, *J. Biol. Chem.* 263:16545–16552. Prior to the present invention, however, the nucleotide sequence of N-proteinase had not been determined and thus the means for producing recombinant N-proteinase was unknown.

III. SUMMARY OF THE INVENTION

N-proteinase exists in two forms, a "short" form comprising a molecule approximately 70 kDa in length and a "long" form comprising a molecule approximately 130 kDa in length. The present invention is directed to polynucleotide sequences encoding both the short and long forms of N-proteinase, including fragments of both forms of N-proteinase having the ability to cleave N-propeptide from procollagen.

The present invention is further directed to synthesized or recombinant compositions corresponding to or derived from the polynucleotide sequences of the present invention. In one embodiment of the present invention, the composition is radiolabelled for use in assays.

The present invention is also related to the synthesis of recombinant production of N-proteinase and related compositions. Where N-proteinase is produced recombinantly, the use of a variety of recombinant expressions systems is contemplated, including yeast, plant cell, insect cell, mammalian cell and *E. coli* expression systems.

IV. DEFINITIONS

As used in this Specification, the term "N-Proteinase" shall mean: (1) a protein encoded by the amino acid sequence as set forth at FIG. 1D (SEQ ID NO:5) deduced from the nucleic acid sequences set forth at FIGS. 1A–1C, (SEQ ID NO:1) a protein encoded by the amino acid sequences as set forth at FIG. 2B (SEQ ID NO:7) deduced from the nucleic acid sequence set forth at FIG. 2A, (SEQ ID NO:6) and the amino acid sequence encoded from the nucleic acid sequences set fort at FIGS. 4A–4B; (SEQ ID NO:8) (2) a protein having N-proteinase activity wherein such protein is encoded by the amino acid sequences deduced from the nucleic acid sequences set forth at FIGS. 1A–1C, (SEQ ID NO:1) FIG. 2A, (SEQ ID NO:6) and FIGS. 4A–4B, (SEQ ID NO:8) wherein one or more amino acids have been added, deleted, mutated, substituted or otherwise altered ("derivative") and the nucleotide sequence encoding said protein can hybridize to the nucleic acid sequence of FIGS. 1A–1C, (SEQ ID NO:1) FIG. 2A (SEQ ID NO:6) and FIGS. 4A–4B (SEQ ID NO:8) under stringent hybridization conditions; (3) a fragment of N-proteinase or a derivative thereof; and (4) the protein encoded by a naturally-occurring allele or homolog of the gene corresponding to the nucleic acid sequences set forth at FIGS. 1A–1C, (SEQ ID NO:1) FIG. 2A, (SEQ ID NO:6) or FIGS. 4A–4B (SEQ ID NO:8).

As used in this Specification, the term "Polynucleotide" denotes DNA, cDNA and/or RNA, including genomic DNA and mRNA.

As used in this Specification, the phrase "Stringent Hybridization Conditions" refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 μg/ml), 0.1% SDS, and 10% dextran sulfate at 42° C., with washes at 42° C. in 0.2 ×SSC and 0.1% SDS.

As used in this Specification, the phrase "Recombinant Expression Vector" refers to a plasmid, virus or other vehicle known in the art that has been manipulated by insertion or incorporation of the N-proteinase sequences.

V. BRIEF DESCRIPTION OF THE DRAWINGS

FIG. 1A sets forth a nucleic acid sequence, positions 1 to 2450, (SEQ ID NO:2) of the 130 kDa ("long") form of human N-proteinase.

FIG. 1B sets forth a nucleic acid sequence, positions 2451 to 4900, (SEQ ID NO:3) of the long form of human N-proteinase.

FIG. 1C sets forth a nucleic acid sequence, positions 4901 to 6692, (SEQ ID NO:4) of the long form of human N-proteinase.

FIG. 1D sets forth the amino acid sequence of the long form of human N-proteinase (SEQ ID NO:5).

FIG. 2A sets forth a nucleic acid sequence of the 70 kDa ("short") form of human N-proteinase (SEQ ID NO:6).

FIG. 2B sets forth the amino acid sequence of the short form of human N-proteinase (SEQ ID NO:7).

FIG. 3 sets forth a schematic comparison of the structure of C-proteinase and N-proteinase and identifies a predicted site for cleavage of the proteinases from their inactive to active forms.

FIG. 4A sets forth a nucleic acid sequence, positions 1 to 2450 (SEQ ID NO:9) of a form of bovine N-proteinase.

FIG. 4B sets forth a nucleic acid sequence, positions 2451 to 4580 (SEQ ID NO:10) of a form of bovine N-proteinase.

FIG. 5 sets forth the deduced amino acid sequence of the bovine N-proteinase (SEQ ID NO:11) set forth in FIGS. 4A and 4B.

FIG. 6 sets forth the oligonucleotide probes used to isolate the nucleic acid molecules encoding bovine N-proteinase (SEQ ID NO:12–17).

VI. DETAILED DESCRIPTION OF THE INVENTION

A. Polynucleotide Sequence Encoding N-Proteinase

Nucleic Acid Sequence Encoding N-Proteinase. The N-proteinase enzyme may be isolated according to the procedures described in Hojima et al., 1989, *J. Biol. Chem.* 264:11336–11345 and Hojima et al., 1994, *J. Biol. Chem.* 269:11381–11390. In one preferred embodiment of the invention, N-proteinase may be further purified by use of monoclonal antibodies obtained by injecting mice with the enzyme purified according to the procedures described in Colige et al., 1995, *J. Biol. Chem.* 270:16724–16730.

The enzyme is amino terminally blocked such that the amino acid corresponding to N-proteinase cannot be determined using a commercially available apparatus. Thus, in one preferred embodiment, the amino acid sequence comprising N-proteinase may be determined by: (1) digesting the enzyme with endoproteinase LysC; (2) resolving the resulting internal peptides by reversed-phase chromatography; and (3) sequencing the material in each of the resultant peaks.

Nucleic acid probes can then be prepared using the determined amino acid sequences for the N-proteinase peptide fragments. Such probes may be synthesized synthetically and labeled. Preparation techniques for such probes and others are generally set forth in Sambrook et al., 1990, *Molecular Cloning, A Laboratory Manual*2d, Ed., Cold Springs Harbor Laboratory Press, New York, at Chapters 10–11. The nucleic acid probes may be sequenced using any one of the techniques generally described in Sambrook et al., supra, at Chapter 13. These nucleic acid probes may be used then to screen a wide array of libraries to isolate and then characterize the full length nucleic acid sequence encoding N-proteinase. For example, the probes may be used to screen a bacteriophage cDNA library or other cDNA library, including libraries constructed using a mammalian expression vector such as pcDNA1 and a genomic library.

The gene encoding N-proteinase may also be isolated by performing a polymerase chain reaction (PCR) using one or more degenerate oligonucleotide primer pools that are designed based on the deduced nucleotide sequence of N-proteinase. The techniques used to identify the nucleic acid sequence of a protein using PCR are described in, for example, Sambrook et al., supra, at Chapter 14.

Nucleic acid sequences encoding N-proteinase have been determined and are set forth at FIGS. 1A–1C (human), (SEQ ID NO:1) FIGS. 2A (human) (SEQ ID NO:6) and 4A–4B (SEQ ID NO:8) (bovine). It is contemplated that the polynucleotide sequences of the present invention include the sequences set forth in FIGS. 1A–1C, FIG. 2A and FIGS. 4A–4B, as well as sequences corresponding to the naturally-occurring alleles and homologs to the disclosed sequence, and variants which are the result of polymorphism.

Other Nucleic Acid Sequences Encoding N-Proteinase. In accordance with the invention, nucleotide sequences encoding N-proteinase or functional equivalents thereof may be used to generate recombinant DNA molecules that direct the expression of the protein or a functional equivalent thereof, in appropriate host cells. Alternatively, nucleotide sequences which hybridize, under stringent hybridization conditions, to portions of the N-proteinase sequence may also be used in nucleic acid hybridization assays, Southern and Northern blot analyses, etc. In yet another method, DNA molecules encoding N-proteinase may be isolated by hybridization procedures comprising antibody screening of expression libraries to detect shared structural features.

Due to the inherent degeneracy of the genetic code, other DNA sequences which encode substantially the same or a functionally equivalent amino acid sequence, may be isolated and used in the practice of the invention for the cloning and expression of N-proteinase. Such DNA sequences include those which are capable of hybridizing to the human or bovine N-proteinase sequence under stringent conditions.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the N-proteinase sequence, which result in a silent change thus producing a functionally equivalent protein. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, aniline; asparagine, glutamine; serine, threonine; phenylalanine, tyrosine.

The DNA sequences of the invention may be engineered in order to alter the protein's sequence for a variety of ends including but not limited to alterations which modify processing and expression of the gene product. For example, mutations may be introduced using techniques which are well known in the art, e.g., site-directed mutagenesis to, for example, insert new restriction sites. For example, in certain expression systems such as yeast, host cells may over-glycosylate the gene product. When using such expression systems it may be preferable to alter N-proteinase coding sequence to eliminate any N-linked glycosylation site.

The N-proteinase sequence may be ligated to a heterologous sequence to encode a fusion protein. For example, a fusion protein may be engineered to contain a cleavage site located between the N-proteinase sequence and a heterologous protein sequence, so that N-proteinase can be cleaved away from the heterologous moiety.

The coding sequence of N-proteinase may also be synthesized in whole or in part, using chemical methods well known in the art. See, for example, Caruthers et al., 1980, *Nucleic Acids Res. Symp. Ser*. 7:215–233; Crea and Horn, 1980, *Nucleic Acids Res*. 9:2331; Matteucci and Caruthers, 1980, *Tetrahedron Letters* 21:719; and Chow and Kempe, 1981, *Nucleic Acids Res*. 9:2807–2817. Alternatively, the protein itself could be produced using chemical methods to synthesize the N-proteinase amino acid sequence in whole or in part. For example, peptides can be synthesized by solid phase techniques, cleaved from the resin, and purified by preparative high performance liquid chromatography. See, e.g., Creighton, 1983, *Proteins Structures And Molecular Principles*, W.H. Freeman and Co., N.Y. pp. 50–60. The composition of the synthetic peptides may be confirmed by amino acid analysis or sequencing. See, e.g., for the Edman degradation procedure, see, Creighton, 1983, *Proteins, Structures and Molecular Principles*, W.H. Freeman and Co., N.Y., pp. 34–49.

B. Uses of the N-Proteinase Coding Sequence

The N-proteinase coding sequence may be used for diagnostic purposes for detection of N-proteinase expression. Included in the scope of the invention are oligoribonucleotide sequences, that include antisense RNA and DNA molecules and ribozymes that function to inhibit translation of N-proteinase. Antisense techniques are known in the art and may be applied herein.

Ribozymes-are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of N-proteinase RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between fifteen (15) and twenty (20) ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

In addition, mutated forms of N-proteinase, having a dominant negative effect, may be expressed in targeted cell populations to inhibit the activity of endogenously expressed wild-type N-proteinase.

Additionally, the DNA encoding N-proteinase may also have a number of uses for the diagnosis of diseases resulting from aberrant expression of the enzyme. For example, the N-proteinase DNA sequence may be used in hybridization assays of biopsies or autopsies to diagnose abnormalities of expression (e.g., Southern or Northern blot analysis, in situ hybridization assays).

The N-proteinase cDNA may be used also as a probe to detect the expression of the N-proteinase mRNA.

In addition, the expression of N-proteinase during embryonic development may also be determined using nucleic acid encoding N-proteinase. As addressed, infra, insufficient production of N-proteinase is the cause of various disease states, including the Ehlers-Danlos disease. See, Section VI.H. In situ hybridizations using N-proteinase as a probe may be employed to predict in utero problems related to such connective tissue diseases. Further, as indicated, infra, administration of human N-proteinase, recombinantly produced as described herein, may be used to treat disease states related to insufficient production of N-proteinase. Alternatively, gene therapy approaches may be employed to remedy deficiencies of functional N-proteinase.

Various modifications to the DNA molecules may be introduced as a means of increasing intracellular stability and half-life. Possible modifications include but are not limited to the addition of flanking sequences of ribo- or deoxynucleotides to the 5' and/or 3' ends of the molecule or the use of phosphorothioate or 2' O-methyl rather than phosphodiesterase linkages within the oligodeoxyribonucleotide backbone.

C. Methods for Making N-Proteinase

Expression of N-Proteinase. In order to express a biologically active N-proteinase, the nucleotide sequence coding for the protein, or a functional equivalent as described above, supra, was inserted into an appropriate expression vector, i.e., a vector which contains the necessary elements for the transcription and translation of the inserted coding sequence.

More specifically, methods which are well known to those skilled in the art can be used to construct expression vectors containing the N-proteinase sequence and appropriate transcriptional/translational control signals. These methods include in vitro recombinant DNA techniques, synthetic techniques and in vivo recombination/genetic recombination. See, e.g., the techniques described in Sambrook et al., 1990, Molecular Cloning: A Laboratory Manual, Cold Spring Harbor Laboratory, N.Y.; and Ausubel et al., 1989, Current Protocols in Molecular Biology, Greene Publishing Associates and Wiley Interscience, N.Y.

A variety of host-expression vector systems may be utilized to express the N-proteinase coding sequence. These include but are not limited to microorganisms such as bacteria transformed with recombinant bacteriophage DNA, plasmid DNA or cosmid DNA expression vectors containing the N-proteinase coding sequence; yeast, including *Pichia pastoris* and *Hansenula polymorpha*, transformed with recombinant yeast expression vectors containing the N-proteinase coding sequence; insect cell systems infected with recombinant virus expression vectors (e.g., baculovirus) containing the N-proteinase coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the N-proteinase coding sequence; or animal cell systems infected with recombinant virus expression vectors (e.g., adenovirus, vaccinia virus, human tumor cells (including HT-1080)) including cell lines engineered to contain multiple copies of the N-proteinase DNA either stably amplified (CHO/dhfr) or unstably amplified in double-minute chromosomes (e.g., murine cell lines). As used herein, it is understood that the term "host-expression vector systems" and more generally, the term "host cells" includes any progeny of the host cell or host-expression vector system. It is further understood that although all progeny may not be identical to the parental cell, as mutations may occur during replication, such progeny are included in the scope of the invention.

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage 8, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the $^{35}$S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of the N-proteinase DNA SV40$^{-}$, BPV- and EBV-based vectors may be used with an appropriate selectable marker.

In bacterial systems, a number of expression vectors may be advantageously selected depending upon the use intended for the expressed N-proteinase. For example, a suitable vector for expression in bacteria includes the T7-based vector as described in Rosenberg et al., 1987, *Gene* 56:125. As further example, when large quantities of N-proteinase are to be produced to screen peptide libraries, vectors which direct the expression of high levels of protein products that are readily purified may be desirable. Such vectors include but are not limited to the *E. coli* expression vector pUR278 (Ruther et al., 1983, *EMBO J.* 2:1791), in which the N-proteinase coding sequence may be ligated into the vector in frame with the lac Z coding region so that a hybrid AS-lac Z protein is produced; pIN vectors (Inouye and Inouye, 1985, *Nucleic Acids Res.* 13:3101–3109; Van Heeke and Schuster, 1989, *J. Biol. Chem.* 264:5503–5509); and the like. pGEX vectors may also be used to express foreign polypeptides such as N-proteinase with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

More generally, where the host is a procaryote, competent cells which are capable of DNA uptake can be prepared from cells harvested after exponential growth and subsequently treated by the $CaCl_2$, or alternatively $MgCl_2$ or RbCl, method using procedures well known in the art.

Where the host cell is a eukaryote, various methods of DNA transfer can be used. These include transfection of DNA by calcium phosphate-precipitates, conventional mechanical procedures, including microinjection, insertion of a plasmid encased in liposomes, or use of virus vectors. Eukaryotic cells may also be cotransformed with DNA sequences encoding the polypeptide of the invention, and a second foreign DNA molecule encoding a selectable phenotype, such as herpes simplex thymidine kinase gene. Another method is to use a eukaryotic viral vector, such as Simian Virus 40 (SV40) or bovine papilloma virus, to transiently infect or transform eukaryotic cells and express protein. See, Eukaryotic Viral Vectors, 1992, Cold Spring Harbor Laboratory, Gluzman, Ed.). Eukaryotic host cells include yeast, mammalian cells, insect cells and plant cells.

In yeast, a number of vectors containing constitutive or inducible promoters may be used. For a review, see, Current Protocols in Molecular Biology, Vol. 2, 1988, Ausubel et al., Ed., Greene Publish. Assoc. and Wiley Interscience, Ch. 13; Grant et al., 1987, Methods in Enzymology, Wu and Grossman, Eds., Acad. Press, N.Y., 153:516–544; Glover, 1986, DNA Cloning, Vol. II, IRL Press, Wash., D.C., Ch 3; Bitter, 1987, Heterologous Gene Expression in Yeast, Methods in Enzymology, Berger and Kimmel, Eds., Acad. Press, N.Y., 152:673–684; and The Molecular Biology of the Yeast Saccharomyces, 1982, Strathern et al., Eds., Cold Spring Harbor Press, Vols. I and II. For example, various shuttle vectors for the expression of foreign genes in yeast have been reported. Heinemann et al., 1989, *Nature* 340:205; Rose et al., 1987, *Gene* 60:237.

In cases where plant expression vectors are used, the expression of the N-proteinase coding sequence may be driven by any of a number of promoters. For example, viral promoters such as the 35S RNA and 19S RNA promoters of CaMV (Brisson et al., 1984, *Nature* 310:511–514), or the coat protein promoter of TMV (Takamatsu et al., 1987, *EMBO J.* 6:307–311) may be used; alternatively, plant promoters such as the small subunit of RUBISCO (Coruzzi et al., 1984, *EMBO J.* 3:1671–1680; Broglie et al., 1984, *Science* 224:838–843); or heat shock promoters, e.g., soybean hsp17.5-E or hsp17.3-B (Gurley et al., 1986, *Mol. Cell. Biol.* 6:559–565) may be used. These constructs can be introduced into plant cells using Ti plasmids, Ri plasmids, plant virus vectors, direct DNA transformation, microinjection, electroporation, etc. For reviews of such techniques, see, e.g., Weissbach and Weissbach, 1988, Methods for Plant Molecular Biology, Academic Press, NY, Section VIII, pp. 421–463; Grierson and Corey, 1988, Plant Molecular Biology, 2d Ed., Blackie, London, Ch. 7–9.

In an insect system, an alternative expression system could be used to express N-proteinase. In one such system, Baculovirus is used as a vector to express foreign genes. The virus then grows in the insect cells. The N-proteinase coding sequence may be cloned into non-essential regions (for example the polyhedron gene) of the virus and placed under control of a Baculovirus promoter. These recombinant viruses are then used to infect insect cells in which the inserted gene is expressed. See, e.g., Smith et al., 1983, *J. Virol.* 46:584; Smith, U.S. Pat. No. 4,215,051.

In mammalian host cells, a number of viral based expression systems may be utilized. In cases where an adenovirus is used as an expression vector, the N-proteinase coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region El or E3) will result in a recombinant virus that is viable and capable of expressing N-proteinase in infected hosts. See, e.g., Logan and Shenk, 1984, *Proc. Natl. Acad. Sci. USA* 81:3655–3659. Alternatively, the vaccinia 7.5K promoter may be used. See, e.g., Mackett et al., 1982, *Proc. Natl. Acad. Sci. USA* 79:7415–7419; Mackett et al., 1984, *J. Virol.* 49:857–864; Panicali et al., 1982, *Proc. Natl. Acad. Sci. USA* 79:4927–4931. Preferably, the vehicle used is a Forest Semiliki Virus.

In another embodiment, the N-proteinase sequence is expressed in human tumor cells, such as HT-1080, which have been stably transfected with calcium phosphate precipitation and a neomycin resistance gene. In yet another embodiment, the pMSXND expression vector or the like is used for expression in a variety of mammalian cells, including COS, BHK, 293 and CHO cells. Lee and Nathans, 1988, *J. Biol. Chem.* 263:3521.

Specific initiation signals may also be required for efficient translation of inserted N-proteinase coding sequences. These signals include the ATG initiation codon and adjacent sequences. In cases where the entire N-proteinase gene, including its own initiation codon and adjacent sequences, is inserted into the appropriate expression vector, no additional translational control signals may be needed. However, in cases where only a portion of the N-proteinase coding sequence is inserted, exogenous translational control signals, including the ATG initiation codon, must be provided. Furthermore, the initiation codon must be in phase with the reading frame of the N-proteinase coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. See, e.g., Bitter et al., 1987, *Methods in Enzymol.* 153:516–544.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, HT-1080, etc.

For long-term, high-yield production of recombinant proteins, stable expression is preferred. For example, cell lines which stably express N-proteinase may be engineered. Rather than using expression vectors which contain viral origins of replication, host cells can be transformed with N-proteinase DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

In addition, it is contemplated that N-proteinase can be co-expressed with collagen or other collagen-related enzymes within the same or different host expression systems such that the expressed N-proteinase can act directly only the second protein (e.g., procollagen).

A number of selection systems may be used, including but not limited to the herpes simplex virus thymidine kinase (Wigler et al., 1977, *Cell* 11:223), hypoxanthine-guanine phosphoribosyltransferase (Szybalska and Szybalski, 1962, *Proc. Natl. Acad. Sci. USA* 48:2026), and adenine phosphoribosyltransferase (Lowy et al., 1980, *Cell* 22:817) genes can be employed in tk, hgprt or aprt cells, respectively.

Also, antimetabolite resistance can be used as the basis of selection for dhfr, which confers resistance to methotrexate (Wigler et al., 1980, *Proc. Natl. Acad. Sci. USA* 77:3567; O'Hare et al., 1981, *Proc. Natl. Acad. Sci. USA* 78:1527); gpt, which confers resistance to mycophenolic acid (Mulligan and Berg, 1981, *Proc. Natl. Acad. Sci. USA* 78:2072); neo, which confers resistance to the aminoglycoside G-418 (Colberre-Garapin et al., 1981, *J. Mol. Biol.* 150:1); and hygro, which confers resistance to hygromycin (Santerre et al., 1984, *Gene* 30:147) genes. Recently, additional selectable genes have been described, namely trpB, which allows cells to utilize indole in place of tryptophan; hisD, which allows cells to utilize histinol in place of histidine (Hartman and Mulligan, 1988, *Proc. Natl. Acad. Sci. USA* 85:8047), and ODC (ornithine decarboxylase) which confers resistance to the ornithine decarboxylase inhibitor, 2-(difluoromethyl)-DL-ornithine, DFMO (McConlogue, 1987, In: *Current Communications in Molecular Biology*, Cold Spring Harbor Laboratory).

The isolation and purification of host cell expressed polypeptides of the invention may be by any conventional means such as, for example, preparative chromatographic separations and immunological separations such as those involving the use of monoclonal or polyclonal antibody.

Identification of Transfectants or Transformants that Express N-Proteinase. The host cells which contain the coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of N-proteinase mRNA transcripts in the host cell; and (d) detection of the gene product as measured by an assay or by its biological activity.

In the first approach, the presence of the N-proteinase coding sequence inserted in the expression vector can be detected by DNA-DNA or DNA-RNA hybridization using probes comprising nucleotide sequences that are homologous to the N-proteinase coding sequence, respectively, or portions or derivatives thereof.

In the second approach, the recombinant expression vector/host system can be identified and selected based upon the presence or absence of certain "marker" gene functions (e.g., resistance to antibiotics, resistance to methotrexate, transformation phenotype, occlusion body formation in baculovirus, etc.). For example, in a preferred embodiment, the N-proteinase coding sequence is inserted within a neomycin-resistance marker gene sequence of the vector, and recombinants containing the N-proteinase coding sequence can be identified by the absence of the marker gene function. Alternatively, a marker gene can be placed in tandem with the N-proteinase sequence under the control of the same or different promoter used to control the expression of the N-proteinase coding sequence. Expression of the marker in response to induction or selection indicates expression of the N-proteinase coding sequence.

In the third approach, transcriptional activity for the N-proteinase coding region can be assessed by hybridization assays. For example, RNA can be isolated and analyzed by Northern blot using a probe homologous to the N-proteinase coding sequence or particular portions thereof. Alternatively, total nucleic acids of the host cell may be extracted and assayed for hybridization to such probes.

The fourth approach involves the detection of the biologically active or immunologically reactive N-proteinase gene product. A number of assays can be used to detect N-proteinase activity including but not limited to those assays described in U.S. Pat. No. 5,408,040.

D. Structure of N-Proteinase

The structural organization of N-proteinase is similar to C-proteinase insofar as the protein is comprised of identifiable domains, which include a large proenzyme domain, an astacin protease-like domain and a large C-terminal region. The structure of N-proteinase, as compared to C-proteinase, is set forth at FIG. 3. Unlike C-proteinase, N-proteinase does not have repetitive CUB and EGF-like domains; rather, a number of regions comprising N-proteinase contain one to four amino acids which are identical in position and identity to the pCP-2 form of C-proteinase.

E. Pharmaceutical Formulations and Routes of Administration

The molecules of the present invention can be administered to a patient in need, alone, or in pharmaceutical compositions where one or more of the molecules are mixed with suitable carriers or excipient(s) at doses to treat or ameliorate a variety of disorders.

Whether the composition is comprised of N-proteinase alone or N-proteinase and additional agents as the active ingredient, such composition is prepared by combining, in a pharmaceutically acceptable carrier substance, e.g., inert gels or liquids, the purified N-proteinase and the other active ingredients.

A therapeutically effective dose further refers to that amount of the compound sufficient to result in amelioration of symptoms. Techniques for formulation and administration of the compounds of the instant application may be found in "Remington's Pharmaceutical Sciences," Mack Publishing Co., Easton, Pa., latest edition.

1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an area requiring N-proteinase, often in a depot or sustained release formulation.

Furthermore, one may administer the drug in a targeted drug delivery system, for example, in a liposome coated with a specific antibody, targeting, for example, cartilage. The liposomes will be targeted to and taken up selectively by the afflicted tissue.

2. Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active molecules into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The molecules may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic molecules of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic molecules may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

3. Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal N-proteinase activity). Such information can be used to more accurately determine useful doses in humans.

A therapeutically effective dose refers to that amount of the molecule hat results in amelioration of symptoms or a prolongation of survival in a patient. Toxicity and therapeutic efficacy of such molecules can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Molecules which exhibit high therapeutic indices are preferred. The data obtained from these cell culture assays and animal studies can be used in formulating a range of dosage for use in human. The dosage of such molecules lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p. 1.

Dosage amount and interval may be adjusted individually to provide plasma levels of the active moiety which are sufficient to maintain the induction effects of N-proteinase, or minimal effective concentration (MEC). The MEC will vary for each compound but can be estimated from in vitro data; for example, the concentration necessary to achieve 50–90% activity of N-proteinase to induce bone growth using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4. Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of disorders or diseases in which the administration of a compound of the present invention is desired to ameliorate either the disease or disorder or symptoms related to such disease or disorder.

F. Assays for Detecting N-Proteinase Activity

Methods for measuring cleavage of N-propeptides by N-proteinase are generally known (for review, see, Kadler et al., 1995, *Methods Enzymol.* 248:756–771). Additionally, a rapid precipitation assay and an electrophoretic assay are useful in detecting and measuring N-proteinase activity, see, Nusgens et al., 1979, *Anal. Biochem.* 95:406–412.

Rapid Precipitation Assay. The rapid precipitation assay provides that the reaction products (procollagen and N-proteinase or N-proteinase-like protein) are precipitated with cold ethanol so that the $^{14}C$-labeled N-propeptides are recovered in the supernatant. More specifically, 10 $\mu$l of type I procollagen (1.3 $\mu$g; 40,000 cpm in 0.1 M Tris-HCl, 0.4 M NaCl, 0.01% $NaN_3$, pH 7.5) in 1.5 ml polypropylene tubes were incubated with 90 $\mu$l of enzyme sample in a the above buffer, pH 7.5, for 1 hour at 35° C. The salt concentration of the reaction mixture was approximately 0.05 M Tris-HCl, 0.15 M NaCl, 5 mM $CaCl_2$, 0.005% Brij 35, and 0.01% $NaN_3$, pH 7.5. To stop the reaction 100 $\mu$l of 15 mM EDTA in 0.15 M Tris-HCl, 0.3 M NaCl, and 0.01% $NaN_3$, pH 7.5 and 100 $\mu$l of chilled 81% ethanol was added. The sample is then vigorously mixed and kept in an ice bath for one (1) hour and then centrifuged at 15,000×g for 15 minutes. The supernatant, approximately 200 $\mu$l, should be withdrawn, added to 5 ml of an aqueous scintillation fluid and counted for 2 minutes in a liquid scintillation counter. In a preferred method, all samples are assayed in duplicate.

Samples without enzyme and samples in which EDTA was added before the reaction gave values of about 400 cpm. Enzyme activity was proportional to the amount of enzyme added and to the time of incubation over the range of 200 to 900 cpm above background. The rapid assay was used to define enzyme units as 1 unit equal to the amount of enzyme that cleaves 1 $\mu$g of type I procollagen in one hour at 35° C. under the standard reaction conditions and assuming that the N-propeptides contain about 10% of the $^{14}C$-label.

Electrophoretic Assay. A 50 or 100 $\mu$l reaction mixture of N-proteinase and type I procollagen is prepared according to the method set forth in the rapid detection assay and the mixture is then incubated at 35° C. for 15 to 180 minutes. The mixture is then mixed with 50 to 100 $\mu$l of 0.25 M Tris-HCl, 4% SDS, 15 mM EDTA, 20% glycerol and 0.002% bromphenol blue with or without 4% 2-mercaptoethanol, pH 6.8. The sample is then heated to 100° C. for five (5) minutes. Unreduced samples are then separated by electrophoresis on a polyacrylamide slab gel comprised of a 3.5% stacking gel and a 4 to 14% polyacrylamide separation gel. For reduced samples, a stacking gel of 3.5% polyacrylamide and a separation gel of 5.5 or 15% polyacrylamide was used. The gels were analyzed with a phosphor storage plate imager.

G. Methods for Identifying Inhibitors of N-Proteinase Activity

Compounds peptides and antibodies which inhibit the activity of N-proteinase may be determined by use of the polypeptides of the present invention. Specifically, the following assay system for N-proteinase may be used to determine the effectiveness of a compound, peptide or antibody to inhibit N-proteinase:

Samples of 1.3 μg of procollagen and potential N-proteinase inhibitors in an assay buffer (90 μl final volume), as described in Hojima et al., 1994, *J. Biol. Chem.* 269:11381–11390, are incubated for ten minutes at room temperature, and 2 μl of the purified N-proteinase (0.19 unit) is added. The samples are then incubated for 60 minutes at 35° C. in a water bath. The enzyme reaction is stopped by the addition of 25 μl of 5×concentrated sample buffer containing 10% β-mercaptoethanol. After SDS-gel electrophoresis in 6% polyacrylamide gels, gels are dried and analyzed by fluorography after exposure to X-ray films for four hours or by scanning with the phosphor storage plate for the quantitation of N-proteinase activity. The enzyme activity is calculated from the amounts of pCα1 and pCα2 polypeptide chains, assuming that the molecular masses 135 kDa and 130 kDa, respectively and corrected for uncleaved proα1 and proα2 chains with masses of 155 kDa and 135 kDa, respectively.

H. Uses of N-Proteinase Polypeptides

Production of Mature Collagen. Recombinantly produced N-proteinase may be used for production of mature collagen in vitro. For example, a procollagen cDNA may be expressed in vitro, and the resulting procollagen processed using recombinantly produced N-proteinase as described herein. Preferably, C-proteinase protein, for example prepared as described in copending U.S. application Ser. No. 08/609,187, filed Mar. 1, 1996, is further employed to achieve cleavage of the C-terminal C-propeptides.

Production of Antibodies to Epitopes of Recombinantly Produced N-Proteinase. Various procedures known in the art may be used for the production of antibodies to epitopes of the recombinantly produced N-proteinase. Such antibodies include but are not limited to polyclonal, monoclonal, chimeric, single chain, Fab fragments and fragments produced by an Fab expression library. Neutralizing antibodies, i.e., those which compete for the catalytic domain of the N-proteinase are especially preferred for diagnostics and therapeutics. Such antibodies may be employed, e.g., for the treatment of fibrosis.

Monoclonal antibodies that bind N-proteinase may be radioactively labeled allowing one to follow their location and distribution in the body after injection. Radioactivity tagged antibodies may be used as a non-invasive diagnostic tool for imaging sites of collagen production associated with a number of diseases including fibrosis, and rheumatoid arthritis.

For the production of antibodies, various host animals may be immunized by injection with the N-proteinase protein including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Monoclonal antibodies to N-proteinase may be prepared by using any technique which provides for the production of antibody molecules by continuous cell lines in culture. These include but are not limited to the hybridoma technique originally described by Kohler and Milstein, 1975, *Nature* 256:495497, the human B-cell hybridoma technique (Kosbor et al., 1983, *Immunology Today* 4:72; Cote et al., 1983, *Proc. Natl. Acad. Sci. USA* 80:2026–2030) and the EBV-hybridoma technique (Cole et al., 1985, *Monoclonal Antibodies and Cancer Therapy*, Alan R. Liss, Inc., pp. 77–96). In addition, techniques developed for the production of "chimeric antibodies" (Morrison et al., 1984, *Proc. Natl. Acad. Sci. USA* 81:6851–6855; Neuberger et al., 1984, *Nature* 312:604–608; Takeda et al., 1985, *Nature* 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce N-proteinase-specific single chain antibodies.

Antibody fragments which contain specific binding sites of N-proteinase may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science* 246:1275–1281) to allow rapid and easy identification of monoclonal Fab fragments with the desired specificity to N-proteinase.

Treatment of Disorders Related to N-Proteinase. Various disease states, such as Ehlers-Danlos disease, results from the insufficient production of N-proteinase in vivo. See, Nusgens et al., 1992, *Nature* 1:214–217. Administration of human N-proteinase to a patient suffering from a disease or disorder caused by the lack of N-proteinase, can therefore ameliorate such disease state.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VII. EXAMPLES

A. Example 1

Characterization of Polynucleotide Molecule Encoding Bovine N-Proteinase

1. Purification of N-Proteinase

N-proteinase (PCI-NP) was isolated according to the following procedure, wherein such procedure was performed at 4° C. or in an ice bath unless otherwise stated:

Step I: Preparation of Bovine Skin Extracts. Skin was collected from fetal calves at the third trimester stage. 250 g of material was ground at liquid nitrogen temperature and homogenized with an Ultra Turrax (8000 rpm) in 500 ml of washing buffer (50 mM sodium cacodylate, pH 7.5, 0.25 M sucrose, 2 mM $CaCl_2$, 2.5 mM NEM, 0.5 mM PMSF, and 0.02% $NaN_3$). After centrifugation (20,000×g for 10 min), the pellet was collected, and the washing procedure was repeated once. Pellets were then suspended in 950 ml of extraction buffer (50 mM sodium cacodylate, pH 7.5, 1 M KCl, 2 mM $CaCl_2$, 0.02% Brij) supplemented with 1.25 mM NEM and 0.25 mM PMSF. After shaking for 18 h at 4° C., the samples were centrifuged for 10 min at 15,000×g. The supernatants were collected, and extraction of the pellets was repeated once.

Step II: Ammonium Sulfate Precipitation. The proteins in the pooled supernatants were precipitated by adding ammonium sulfate at 40% saturation. The solution was stirred 18 h at 4° C. and centrifuged at 15,000×g for 30 min. The precipitate was dissolved in extraction buffer and dialyzed.

Step III. Affinity Chromatography on Concanavalin A-Sepharose. The sample was loaded on a 300-ml concanavalin A-Sepharose (Pharmacia LKB Biotechnology, Uppsala, Sweden) column and extensively washed with the extraction buffer. Elution was carried out in the same buffer containing 0.5 M α-methyl-D-mannoside. Active fractions were pooled and dialyzed against buffer H (50 mM sodium cacodylate, pH 7.5, 0.2 M NaCl, 2 M $CaCl_2$, 0.02% Brij).

Step IV: Chromatography on Heparin-Sepharose. The enzyme preparation from step III was applied to a 75-ml heparin-Sepharose (Pharmacia) column equilibrated in buffer H. After washing, elution was performed with a linear gradient prepared from 250 ml of buffer H and 250 ml of buffer H containing 0.95 M KCl. The most active fractions, eluting between 0.6 and 0.8 M KCl, were pooled and dialyzed against TCNa buffer (50 mM Tris, pH 7.5, 0.2 M NaCl, 2 mM $CaCl_2$).

The resulting enzyme was approximately purified 90-fold, with a recovery level of approximately 45%. Attempts to further purify N-proteinase using various chromatographic techniques were unsuccessful to the extent that poor enzyme recovery was observed. Consequently, a monoclonal antibody was developed to further purify the enzyme.

2. Production of Monoclonal Antibody and Further Purification of N-Proteinase

The enzymatic preparation after the heparin-Sepharose chromatography (step IV, above at Section VII.A.1.) was used for immunization of F1 mice (Balb/c×C57 Black/6, Studie Centrum voor Kernenergie, Mol, Belgium). Mice were intraperitoneally inoculated twice at 3-week intervals with 20 μg of antigen emulsified I Freund's adjuvant. Ten days after the second injection, the animals were boosted with 20 μg of antigen in saline and sacrificed 3 days later. Three-thousand (3000) hybridoma clones were screened for their ability to produce a monoclonal antibody able to immunoprecipitate N-proteinase activity in the presence of goat anti-mouse IgG coupled to agarose beads (Sigma). Only one hybridoma supernatant (clone 37D9) out of 3000 promoted significant and reproducible immunoprecipitation. The secreted monoclonal antibody was subclassed as an IgG1. After purification on a protein G column, 20 mg of antibody was coupled to 15 ml of Affi-Gel Hz hydrazide following instructions of the manufacturer (Bio-Rad) with an efficiency of 80% and used to further purify the enzyme as follows:

Step V: Affinity Chromatography on Immobilized 37D9 Monoclonal Antibody. A maximum of 50 ml of the preparation at step IV was applied to an affinity column prepared as described below. After two successive washings in TCNa buffer and in 0.2 M ammonium acetate ($NH_4Ac$), the enzyme was eluted with 0.6 M $NH_4Ac$.

Step VI: Second Chromatography on Heparin-Sepharose. The fractions collected in step V containing the enzymatic activity were pooled and loaded on a 0.5-ml heparin-Sepharose column. After washing in 0.8 M $NH_4Ac$, [PCI-NP was eluted at 1.2 M $NH_4Ac$,] PCI-NP was eluted at 1.2 M $NH_4Ac$ and stored at −80° C.

3. Determination of Amino Acid Sequence Encoding N-Proteinase

Amino-terminal sequence analysis of the intact protein and the peptides was performed on the model 476A protein sequencer (ABI, Foster City, Calif.) operating in the pulsed liquid mode with on-line phenylthiohydantoin analysis. The amino-terminal sequence analysis of the blotted PCI-NP was performed in a cross-flow reaction cartridge using modified run cycles. For sequence analysis of the peptides, trifluoroacetic acid-treated glass fiber disk was covered with polybrene before application of the sample. It was determined, using this method that the amino-terminal amino acid of PCI-NP was blocked and could not be subjected to an amino-terminal sequence analysis by Edman degradation. To overcome this problem, internal peptides of membrane-bound enzyme were produced and analyzed. More specifically, about 10 pmol (1 μg) of the blotted PCI-NP protein indicated that the protein was amino-terminally blocked, we cleaved the membrane-bound protein (30 μg) enzymatically to obtain sequence information for some internal peptide fragments. Endoproteinase Lys-C, which cleaves specifically at the carboxyl-terminal end of every lysyl residue, was chosen because the lysine content in PCI-NP (4%) seemed appropriate to obtain peptides of various lengths that could be easily resolved by reverse phase liquid chromatography analysis. A control digest was performed on a blank piece of PVDF (Coomassie stained but containing no protein) to identify peaks originating from background or enzyme autoproteolysis. After extraction, the peptides were separated on a reverse phase liquid chromatography column containing a mix of $C_2/C_{18}$ chains, and different fractions were collected. Several peptides were subjected to amino-terminal sequence analysis (¾ of the material), but only two fractions, K1 and K3, contained a pure peptide that could be unambiguously sequenced up to the final lysyl residue. Three other fractions contained a mix of two or more fragments or had a very low initial sequence yield (<1 pmol). As a final control, the remainder (¼) of the sequenced fractions was subjected to matrix-assisted laser desorption/ionization mass analysis to verify the obtained sequences. For fraction K3, the calculated mass, 1633.7 Da, is in perfect agreement with the experimentally determined one, 1633.2 Da. Fraction K1 yielded no mass probably because there was too little material left.

The sequences for K1 and K3 were used to screen protein and nucleic acid data banks. No significant homology with known sequences was observed.

4. Cloning and Characterization of Nucleic Acid Sequence Corresponding to N-Proteinase A bovine cDNA library was constructed using degenerated oligonucleotide primers, as set forth as OP 8 (SEQ ID NO:17) and OP 11 (SEQ ID NO:14) at FIG. 6. These primers were designed from partial amino acid sequences reported in Colige et al., 1995, *J. Biol. Chem.* 270:16724–16730. The clones containing N-proteinase cDNA were identified after screening the bovine cDNA library with the longer degenerated oligonucleotides, OP 1 (SEQ ID NO:16) and OP 10, (SEQ ID NO:13) also as set forth in FIG. 6. The bovine nucleotide sequence with the ATG start coding and the TAA stop codon (underlined) is set forth at FIGS. 4A and 4B (SEQ ID NO:8). The deduced amino acid sequence, including the sequence's identifiable domain is set forth in FIG. 5 (SEQ ID NO:11).

5. Isolation of cDNAs for Human N-Proteinase

Total RNA was isolated from human skinfibroblast (CRL 1262) and reverse transcribed with oligo-dT and random primers to cDNA (Pharmacia cDNA synthesis kit). The cDNA then inserted into lambda phage vector ZAP II to make cDNA library. The cDNA library was screened for N-proteinase with $^{32}$P-labeled bovine N-proteinase cDNA probe. Nine cDNA clones (size from 2 kb to 5 kb) were isolated from the library and sequenced with a fluorescent amplicycel sequencer (Perkin Elmer). According to the sequence, the full-length cDNA for human N-proteinase was generated.

6. Cloning of Nucleic Acid Sequence Corresponding to Human N-Proteinase

Overlapping cDNA fragments were obtained by RT-PCR using oligonucleotide primers specific of human N-proteinase and RNA purified from four different strains of skin fibroblasts in culture. Sequences of the cDNA were determined using specific oligonucleotide primers and Thermo Sequence radiolabeled cycle sequencing kit (Amersham).

B. Example 2

Characterization of Polynucleotide Molecule Encoding Human N-Proteinase

The nucleotide sequence of human N-proteinase, both in its long and short form are set forth at FIGS. 1A–1C (SEQ ID NO:1) and FIG. 2A (SEQ ID NO:6). As set forth in FIG. 3, N-proteinase and C-proteinase are similar in structure.

All references cited within the body of the instant specification are hereby incorporated by reference in their entirety

What is claimed:

1. An isolated polynucleotide sequence encoding a polypeptide comprising the amino acid sequence of SEQ ID NO:5 or a fragment thereof having N-proteinase activity.

2. An isolated polynucleotide sequence which is complementary to the polynucleotide sequence of claim 1.

3. An isolated polynucleotide sequence that hybidizes to the polynucleotide of claim 1 or a complement thereof under the following conditions: 0.015 M NaCl, 0.015 M sodium citrate, 0.1% sodium dodecyl sulfate at 50° C.

4. An expression vector comprising the polynucleotide sequence of claim 1, 2, or 3.

5. A host cell comprising the expression vector of claim 4.

6. The host cell of claim 5, wherein the host cell is selected from the group consisting of yeast cells, insect cells, bacterial cells, plant cells, or mammalian cells.

7. A method of producing a polypeptide, the method comprising;

a) culturing the host cell of claim 5 under conditions suitable for the expression of the polypeptide; and b) isolating the polypeptide.

8. An isolated polynucleotide sequence comprising SEQ ID NO:1 or a fragment thereof encoding a polypeptide having N-proteinase activity.

9. An isolated polynucleotide sequence which is complementary to the polynucleotide sequence of claim 8.

10. The host cell of claim 5, wherein the host cell is a eukaryotic host cell.

11. The host cell of claim 5, wherein the host cell is a prokaryotic host cell.

12. A composition comprising the polynucleotide of claim 1.

13. The polynucleotide of claim 1, wherein the polynucleotide comprises the nucleic acid sequence of SEQ ID NO:1 or a fragment or derivative thereof encoding a polypeptide having N-proteinase activity.

14. An isolated and purified polynucleotide comprising a nucleic acid selected from the group consisting of SEQ ID NO:2, SEQ ID NO:3, SEQ ID NO:4, or fragments thereof encoding a polypeptide having N-proteinase activity.

* * * * *

SEQUENCE LISTING

```
(1) GENERAL INFORMATION:

   (iii) NUMBER OF SEQUENCES: 17


(2) INFORMATION FOR SEQ ID NO:1:

     (i) SEQUENCE CHARACTERISTICS:
          (A) LENGTH: 6692 base pairs
          (B) TYPE: nucleic acid
          (C) STRANDEDNESS: single
          (D) TOPOLOGY: linear

           (xi) SEQUENCE DESCRIPTION: SEQ ID NO:1:

GCCCCAGATG TGGGCTGGGC GGCTCGCGGG GAACTTTCGC GCCGGCTGCG AGTGCGGGGC    60

CCCGGCTGCA GTCCGGCTGC CATGGATCCG CCGGCGGGAG CCGCTCGCCG CCTGCTCTGC   120

CCCGCGCTGC TGCTGCTGCT GCTGCTGCTG CCGCCGCCGC TCCTGCCGCC GCCGCCGCCG   180

CCCGCGAACG CCAGGCTCGC CGCCGCCGCC GACCCCCCAG GCGGGCCCCT GGGGCACGGA   240

GCGGAGCGCA TCCTGGCGGT GCCCGTGCGC ACTGACGCCC AGGGCCGCTT GGTGTCCCAC   300

GTGGTGTCGG CAGCTACGTC CAGAGCAGGG GTACGAGCCC GCAGGGCCGC CCCGGTCCGG   360

ACCCCGAGCT TCCCCGGAGG CAACGAGGAG GAGCCTGGCA GTCACCTCTT CTACAATGTC   420

ACGGTCTTTG GCCGAGACCT GCACCTGCGG CTGCGGCCCA ACGCCCGCCT CGTGGCGCCC   480

GGGGCCACTA TGGAGTGGCA GGGCGAGAAG GGCACCACCC GCGTGGAGCC CCTGCTCGGG   540

AGCTGTCTCT ACGTCGGAGA CGTGGCCGGC CTAGCCGAAG CCTCCTCTGT GGCGCTCAGC   600

AACTGCGATG GGCTGGCTGG TCTGATCCGG ATGGAGGAGG AGGAGTTCTT CATCGAACCC   660

TTGGAGAAGG GGCTGGCGGC GCAGGAGGCT GAGCAAGGCC GTGTGCATGT GGTGTATCGC   720

CGGCCACCCA CGTCCCCTCC TCTCGGGGGG CCACAGGCCC TGGACACAGG GGCCTCCCTG   780

GACAGCCTGG ACAGCCTCAG CCGCGCCCTG GGCGTCCTAG AGGAGCACGC CAACAGCTCG   840

AGGCGGAGGG CACGCAGGCA TGCTGCAGAC GATGACTACA ACATCGAGGT CCTGCTGGGC   900

GTGGATGACT CTGTGGTGCA GTTCCACGGG AAGGAGCACG TACAGAAGTA CCTGCTGACA   960

CTCATGAACA TTGTCAATGA AATCTACCAT GACGAGTCCT TGGGTGCCCA CATCAACGTG  1020

GTCCTGGTGC GGATCATCCT CCTGAGCTAT GGAAAGTCCA TGAGCCTCAT CGAGATCGGG  1080

AACCCCTCTC AGAGCCTGGA GAATGTCTGC CGCTGGGCCT ACCTCCAGCA GAAGCCAGAC  1140

ACGGGCCACG ATGAATACCA CGATCACGCC ATCTTCCTCA CACGGCAGGA CTTTGGGCCT  1200

TCCGGCATGC AAGGCTATGC TCCTGTCACC GGCATGTGCC ATCCGGTCCG CAGCTGCACC  1260
```

-continued

```
CTGAACCATG AGGACGGCTT CTCCTCAGCG TTTGTGGTGG CCCATGAGAC TGGCCACGTG  1320
CTGGGCATGG AGCACGACGG GCAGGGCAAC CGCTGTGGCG ACGAGGTGCG GCTGGGCAGC  1380
ATCATGGCGC CCCTGGTGCA GGCCGCCTTC CACCGCTTCC ACTGGTCCCG CTGCAGCCAG  1440
CAGGAGCTGA GCCGCTACCT GCACTCCTAT GACTGCCTGC TGGATGACCC CTTCGCCCAC  1500
GACTGGCCGG CGCTGCCCCA GCTCCCGGGA CTGCACTACT CCATGAACGA GCAATGCCGC  1560
TTTGACTTCG GCCTGGGCTA CATGATGTGC ACGGCGTTCC GGACCTTTGA CCCCTGCAAG  1620
CAGCTGTGGT GCAGCCATCC TGACAACCCC TACTTTTGCA AGACCAAGAA GGGGCCCCCC  1680
TTGGACGGGA CTATGTGTGC ACCTGGCAAG CATTGTTTTA AAGGACACTG CATCTGGCTG  1740
ACACCTGACA TCCTCAAACG GGACGGCAGC TGGGGCGCTT GGAGTCCGTT TGGCTCCTGC  1800
TCACGTACCT GTGGCACGGG CGTGAAGTTC AGGACCCGCC AGTGTGACAA CCCACACCCG  1860
GCCAACGGGG GCCGCACCTG CTCGGGCCTT GCCTACGACT TCCAGCTCTG CAGCCGCCAG  1920
GACTGCCCCG ACTCCCTGGC TGACTTCCGC GAGGAGCAGT GCCGCCAGTG GGACCTGTAC  1980
TTCGAGCACG GCGACGCCCA GCACCACTGG CTGCCCCACG AGCACCGGGA TGCCAAGGAG  2040
AGATGCCACC TGTACTGCGA GTCCAGGGAG ACCGGGGAGG TGGTGTCCAT GAAGCGCATG  2100
GTGCATGATG GGACGCGCTG CTCCTACAAG GACGCCTTCA GCCTCTGTGT GCGCGGGGAC  2160
TGCAGGAAGG TGGGCTGTGA CGGTGTGATC GGCTCCAGCA AGCAGGAAGA CAAGTGTGGC  2220
GTGTGCGGAG GGGACAACAG CCACTGCAAA GTGGTCAAGG GCACGTTCAC ACGGTCACCC  2280
AAGAAGCATG GTTACATCAA GATGTTTGAG ATCCCTGCAG GAGCCAGACA CCTGCTCATT  2340
CAGGAGGTAG ACGCCACCAG CCACCATCTG GCCGTCAAGA ACCTGGAGAC AGGCAAGTTC  2400
ATCTTAAATG AAGAGAATGA CGTGGATGCC AGTTCCAAAA CCTTCATTGC CATGGGCGTG  2460
GAGTGGGAGT ACAGAGACGA GGACGGCCGG GAGACGCTGC AGACCATGCG CCCCCTCCAC  2520
GGCACCATCA CCGTTCTGGT CATCCCGGTG GGAGACACCC GGGTCTCACT GACGTACAAA  2580
TACATGATCC ATGAGGACTC ACTGAATGTC GATGACAACA ACGTCCTGGA AGAGGACTCT  2640
GTGGTCTAGG AGTGGGCCCT GAAGAAGTGG TCTCCGTGCT CCAAGCCCTG TGGCGGAGGG  2700
TCCCAGTTCA CCAAGTATGG CTGCCGCCGG AGGCTGGACC ACAAGATGGT ACACCGTGGC  2760
TTCTGTGCCG CCCTCTCGAA GCCCAAAGCC ATCCGCAGAG CGTGCAACCC ACAGGAATGC  2820
TCCCAGCCAG TGTGGGTCAC AGGCGAATGG GAGCCATGTA GCCAGACCTG TGGGCGGACA  2880
GGCATGCAGG TGCGCTCCGT GCGCTGCATT CAGCCGCTAC ACGACAACAC CACCCGCTCC  2940
GTGCACGCCA AGCACTGCAA TGACGCCCGG CCCGAGAGCC GCCGGGCCTG CAGCCGCGAG  3000
CTCTGCCCTG GTCGTTGGCG AGCCGGGCCC TGGTCCCAGT GCTCAGTAAC CTGTGGCAAC  3060
GGCACCCAGG AGCGGCCAGT GCTCTGCCGC ACCGCGGACG ACAGCTTCGG CATCTGCCAG  3120
GAGGAGCGTC CTGAGACAGC GAGGACCTGC AGGCTTGGCC CCTGTCCCCG AAACATCTCA  3180
GATCCCTCCA AGAAGAGCTA CGTAGTTCAG TGGCTGTCCC GCCCGGACCC CGACTCGCCC  3240
ATCCGGAAGA TCTCGTCAAA GGGCCACTGC CAAGGCGACA AGTCAATATT CTGTAGGATG  3300
GAAGTCTTGT CCCGCTATTG CTCCATCCCA GGCTACAACA AGCTGTGCTG CAAGTCCTGT  3360
AACCTGTACA ACAACCTCAC CAACGTGGAG GGCAGGATAG AGCCACCGCC TGGGAAGCAC  3420
AACGACATTG ACGTGTTCAT GCCTACCCTC CCAGTGCCCA CTGTAGCCAT GGAGGTGCGG  3480
CCATCACCAA GCACCCCCCT GGAGGTCCCT CTCAATGCCT CCAGCACCAA TGCCACAGAG  3540
GATCACCCAG AAACCAATGC CGTAGATGAA CCCTACAAAA TCCATGGCCT GGAAGATGAA  3600
```

-continued

```
GTCCAGCCAC CCAACCTAAT CCCTCGACGA CCGAGCCCCT ATGAAAAGAC CAGAAACCAA  3660

AGAATCCAAG AGCTCATTGA TGAGATGCGG AAGAAAGAGA TGCTCGGAAA GTTCTAATAA  3720

AATGGAAAGA TAGCATCCCT AGCATTTTTT TCTTGCTTAT AGAGATATTC CATGGGATAG  3780

CAAATCCTGT GTCATGGAGA TGAAGTCAAA ATTCCTGATT CCAAAAGGTT TTGAGAAAAC  3840

AAAGAGGGGG AATGACGTAA GAAAGATACG CATGAGCATG TGGTAAGCTA GGTTAGCACG  3900

TGTGCTTCCC AGCCCAGGAG CGACCAAATA CTGTGGTGGC GTCAGGTGTG CACTGGAGAG  3960

GAATATAGAG GCTGTATGGC CTCCCTCACT GAGGGCAGGG CAAGAGGGAT CACTCTACAA  4020

ACAAAAATAG GCCCCAAGTT GCTAAGCAGT GATTGGGAAC CTTCCTTTCC TTGGCGGAGA  4080

TGCATGACAT TCCCTACCGA TCCCCAGACA CAGCCTGTGG CAGTCTTAGG AGAAATGGTG  4140

ATTTACTGAA TAACTGACCC GTTGCCGAGA TGAGTACAAT GAAGTGGAGG TGATGAACTC  4200

AAATCGTCTT CCAGGGCCAG GCGGCTGACC GGGGTGAGCG TAGTGGCCCG CTGGGGACCA  4260

TGGCCGCCCT GACAGCCACA CCCACCTGGA GCTGACTTGG TTCTGGCTGT TGCTGCCACT  4320

GTGAAATCTG TATCTCTCTC CATCTCTGCT CTACTATCCC CGGCCTTGCC AGACAGTGTT  4380

CTTTTTCGGA AGAAGTCTAG ATTTTTGCAT GAAAAAAACT CAATCTTTAA AGGTCGACTC  4440

AGAACATTTT AAGGAGGCCT CCACTTGGTC TGATGCAGTC TTGCTAATTA AGAACTAAAA  4500

GGCTTCTGAC CTTCTTGGTG CTCATGCTGT ACGGCATCTG AATGTCTCGA CCGAGTCTGA  4560

GCCGTGCAGC TGTCCTCCAC CTGCGAAAGT AATGAGAATC CTATCACGGG ACATAAGGAT  4620

AGGTCTAAAC AGGGTCCATG CCAAGAAAAC AGTGGGGTGC TCTCCCAGGC CTCTCCCCTG  4680

TCCACTAACC CTGGCCTTGC CGGCTGCCTT CCAGGCTCTG GGGGAAGAGC TCCTGCATTC  4740

TTCCCTGGCC ACCTTGGCTC CAGGGCTCCC CAAGAGCCTC TTCCCTCCCC AAGTACCTGA  4800

GAAAGATGAG AGAGGCACGT GCTCTGCTGG GAAGGTCCAG TGAGCGGTTC AAGGGCCTGG  4860

AATCTCCCTA CGGCCAAGTC TAAGGGTTCT GGGATTCTGG GCTTTGTGGG CTTTGCTTGC  4920

TTGCTGGGAA TGGGCTTTCC CTGTCCCGCC TGCCCCACTT GCTTTGTTTT CAGAAGCTCC  4980

AGAACCCAGC AGTGACTGCA AAATGTGGCT TGATGGGGGC TTAGGGTGGG AGATGGGGAG  5040

AGCTACATTG TCTTTTGCTC CTTGAAAACT TTAATAGCTC CTATTTTCCA GAGAATGGTG  5100

CTTTGTGAGC AACATGCGAG TAAGAGAGAA ATAGGAGGAA GGGGGAGTAG GGGCGGATGG  5160

GAGAAGAGTG GCTCATTTTT ACCTCTCACT GCCTGACATT TTGTGAACGT GAAGCTTAAA  5220

CTTTCTGGGC TTACAAGACC CAGGGGCACG TCAGCTCCTT AGATGGGCTC AGCCTGACAC  5280

ATAATTCTTA AACCTTTCCT GTTTAAGAAA CTTCTAGAGG CTGTGTACTC TCACCAATCC  5340

TCTTCGAGAA TTTGTTCATG TGTATTTCCC CATTATATGG ATGAGGCTCA GGATAACAGC  5400

ATAGTGGCTA CCTTCTACTG AGTTTTGAGG TGCTAATAAG TATGTTTGTC TGAGGCTGCA  5460

CATGTGGGTG GCTCTGTGTG TATGATCCAA GGGACAAAAT GACGATGTAG AACCAGCAAG  5520

AACGGAATCT GGGCTGATGC TTCAGTCTCC ACCTGGGTGA TGGTAGCCTC CCGCCCTCCA  5580

CCACCGCATC CCACACGTGC TGCGCACTGT CCCCGTGTCT CCTGGAGAAC CAAACTGGAG  5640

AAAACCTTTC TGAGTATCTC TCATAGTACC CCTTCCTTAA GAAGATGTGG TTTAGAGCAT  5700

GTGTGCAATC CTGCCTCTGT AATTAGGAAA CGGAGCCCGA GGCTTTCCAT TGTTGGTTGA  5760

ACCCAGGACA GCTGGTGCTA TTCACAGGCT GAAGAACTGG GCAGTTCTTA CTTGGGTCTG  5820

TCCTAGGATG TGGAGGAAGT TCAGGACTAA CGCTAGGCAG AGAGTATGAC TCGGTTTACC  5880

CAGCCTAGGG GCCTCTGGAT GGGAACACTC CATTCCAAGA TCTCAGCAGA GCAGGGCTTC  5940

CTGGCTTGAG GCTGGAAGCC TTTGGGAAGA GGCCCAGCTG GACATTACC  TGGCACCTTC  6000
```

```
TTCCCGTTGA AGGGAGCAAG GTGCCCTCTG GGATGACAGC CAGACCCTTG TGCCATCCTC  6060

AATCTTGAGC CATATATCAA GAGTCCTCTA GAGCCGGATG GTCCTCAAAA GTCTGTCCAA  6120

GGAATGCCAA CGTTCACCGG GCTTGAGAAA CGACGCAAAT CTCTGAGCTG GGGACCACTT  6180

GGAGAACCGG CTTAGTAACA GTCCTGATCT TCGCAAGCCA GTTGTTGTGC ATCTGAGGGG  6240

CTCCTGGCGC CCAGAGGAGG CAGACAGATG CTTCTAGCTG AGTTTCTAAC CGCATGATGA  6300

GACTCAGACC TTCCGCTGCA TAGAAAATTG CAACAGTGTC CGGAGTCATT TTTCCTTAGT  6360

GGGCAGACTC GTGTTAGATT TGGGAACCCA GCTCTTGATT ACTCCTTTTG GAAAACCCAT  6420

GGAATTTCAT GTATAAGGCT TTCATTTGTA TTTTAAGGTT TTTTGTTTGT TTGAGTATAA  6480

CATGGTGCTC AATAGCAACA TCTTAGCAGA TGAAGCAGTT TATGATTCCA CTCCCTCCTG  6540

TATGACAGGT AGCCACTATA CTGAATCAAG GTGCTGAACT CAAATCACAA AATTCTGGCT  6600

TACCGATACA ACAACCAATA CATCTTTGTT TGTAATAAAA AATTTGACTC CTTACTTTTA  6660

TAACTTATTA AAGTTAAAAT GTCTGTGTTT TT                                6692
```

(2) INFORMATION FOR SEQ ID NO:2:

(i) SEQUENCE CHARACTERISTICS:
(A) LENGTH: 2450 base pairs
(B) TYPE: nucleic acid
(C) STRANDEDNESS: single
(D) TOPOLOGY: linear (xi) SEQUENCE DESCRIPTION: SEQ ID NO:2:

```
GCCCCAGATG TGGGCTGGGC GGCTCGCGGG GAACTTTCGC GCCGGCTGCG AGTGCGGGGC    60

CCCGGCTGCA GTCCGGCTGC CATGGATCCG CCGGCGGGAG CCGCTCGCCG CCTGCTCTGC   120

CCCGCGCTGC TGCTGCTGCT GCTGCTGCTG CCGCCGCCGC TCCTGCCGCC GCCGCCGCCG   180

CCCGCGAACG CCAGGCTCGC CGCCGCCGCC GACCCCCCAG GCGGGCCCCT GGGGCACGGA   240

GCGGAGCGCA TCCTGGCGGT GCCCGTGCGC ACTGACGCCC AGGGCCGCTT GGTGTCCCAC   300

GTGGTGTCGG CAGCTACGTC CAGAGCAGGG GTACGAGCCC GCAGGGCCGC CCCGGTCCGG   360

ACCCCGAGCT TCCCCGGAGG CAACGAGGAG GAGCCTGGCA GTCACCTCTT CTACAATGTC   420

ACGGTCTTTG GCCGAGACCT GCACCTGCGG CTGCGGCCCA ACGCCCGCCT CGTGGCGCCC   480

GGGGCCACTA TGGAGTGGCA GGGCGAGAAG GGCACCACCC GCGTGGAGCC CCTGCTCGGG   540

AGCTGTCTCT ACGTCGGAGA CGTGGCCGGC CTAGCCGAAG CCTCCTCTGT GGCGCTCAGC   600

AACTGCGATG GGCTGGCTGG TCTGATCCGG ATGGAGGAGG AGGAGTTCTT CATCGAACCC   660

TTGGAGAAGG GGCTGGCGGC GCAGGAGGCT GAGCAAGGCC GTGTGCATGT GGTGTATCGC   720

CGGCCACCCA CGTCCCCTCC TCTCGGGGGG CCACAGGCCC TGGACACAGG GGCCTCCCTG   780

GACAGCCTGG ACAGCCTCAG CCGCGCCCTG GGCGTCCTAG AGGAGCACGC CAACAGCTCG   840

AGGCGGAGGG CACGCAGGCA TGCTGCAGAC GATGACTACA ACATCGAGGT CCTGCTGGGC   900

GTGGATGACT CTGTGGTGCA GTTCCACGGG AAGGAGCACG TACAGAAGTA CCTGCTGACA   960

CTCATGAACA TTGTCAATGA AATCTACCAT GACGAGTCCT TGGGTGCCCA CATCAACGTG  1020

GTCCTGGTGC GGATCATCCT CCTGAGCTAT GGAAAGTCCA TGAGCCTCAT CGAGATCGGG  1080

AACCCCTCTC AGAGCCTGGA GAATGTCTGC CGCTGGGCCT ACCTCCAGCA GAAGCCAGAC  1140

ACGGGCCACG ATGAATACCA CGATCACGCC ATCTTCCTCA CACGGCAGGA CTTTGGGCCT  1200

TCCGGCATGC AAGGCTATGC TCCTGTCACC GGCATGTGCC ATCCGGTCCG CAGCTGCACC  1260

CTGAACCATG AGGACGGCTT CTCCTCAGCG TTTGTGGTGG CCCATGAGAC TGGCCACGTG  1320
```

-continued

```
CTGGGCATGG AGCACGACGG GCAGGGCAAC CGCTGTGGCG ACGAGGTGCG GCTGGGCAGC  1380

ATCATGGCGC CCCTGGTGCA GGCCGCCTTC CACCGCTTCC ACTGGTCCCG CTGCAGCCAG  1440

CAGGAGCTGA GCCGCTACCT GCACTCCTAT GACTGCCTGC TGGATGACCC CTTCGCCCAC  1500

GACTGGCCGG CGCTGCCCCA GCTCCCGGGA CTGCACTACT CCATGAACGA GCAATGCCGC  1560

TTTGACTTCG GCCTGGGCTA CATGATGTGC ACGGCGTTCC GGACCTTTGA CCCCTGCAAG  1620

CAGCTGTGGT GCAGCCATCC TGACAACCCC TACTTTTGCA AGACCAAGAA GGGGCCCCCC  1680

TTGGACGGGA CTATGTGTGC ACCTGGCAAG CATTGTTTTA AAGGACACTG CATCTGGCTG  1740

ACACCTGACA TCCTCAAACG GGACGGCAGC TGGGGCGCTT GGAGTCCGTT TGGCTCCTGC  1800

TCACGTACCT GTGGCACGGG CGTGAAGTTC AGGACCCGCC AGTGTGACAA CCCACACCCG  1860

GCCAACGGGG GCCGCACCTG CTCGGGCCTT GCCTACGACT TCCAGCTCTG CAGCCGCCAG  1920

GACTGCCCCG ACTCCCTGGC TGACTTCCGC GAGGAGCAGT GCCGCCAGTG GGACCTGTAC  1980

TTCGAGCACG GCGACGCCCA GCACCACTGG CTGCCCCACG AGCACCGGGA TGCCAAGGAG  2040

AGATGCCACC TGTACTGCGA GTCCAGGGAG ACCGGGGAGG TGGTGTCCAT GAAGCGCATG  2100

GTGCATGATG GGACGCGCTG CTCCTACAAG GACGCCTTCA GCCTCTGTGT GCGCGGGGAC  2160

TGCAGGAAGG TGGGCTGTGA CGGTGTGATC GGCTCCAGCA AGCAGGAAGA CAAGTGTGGC  2220

GTGTGCGGAG GGGACAACAG CCACTGCAAA GTGGTCAAGG GCACGTTCAC ACGGTCACCC  2280

AAGAAGCATG GTTACATCAA GATGTTTGAG ATCCCTGCAG GAGCCAGACA CCTGCTCATT  2340

CAGGAGGTAG ACGCCACCAG CCACCATCTG GCCGTCAAGA ACCTGGAGAC AGGCAAGTTC  2400

ATCTTAAATG AAGAGAATGA CGTGGATGCC AGTTCCAAAA CCTTCATTGC             2450
```

(2) INFORMATION FOR SEQ ID NO:3:

(i) SEQUENCE CHARACTERISTICS:
(A) LENGTH: 2450 base pairs
(B) TYPE: nucleic acid
(C) STRANDEDNESS: single
(D) TOPOLOGY: linear (xi) SEQUENCE DESCRIPTION: SEQ ID NO:3:

```
CATGGGCGTG GAGTGGGAGT ACAGAGACGA GGACGGCCGG GAGACGCTGC AGACCATGCG    60

CCCCCTCCAC GGCACCATCA CCGTTCTGGT CATCCCGGTG GGAGACACCC GGGTCTCACT   120

GACGTACAAA TACATGATCC ATGAGGACTC ACTGAATGTC GATGACAACA ACGTCCTGGA   180

AGAGGACTCT GTGGTCTAGG AGTGGGCCCT GAAGAAGTGG TCTCCGTGCT CCAAGCCCTG   240

TGGCGGAGGG TCCCAGTTCA CCAAGTATGG CTGCCGCCGG AGGCTGGACC ACAAGATGGT   300

ACACCGTGGC TTCTGTGCCG CCCTCTCGAA GCCCAAAGCC ATCCGCAGAG CGTGCAACCC   360

ACAGGAATGC TCCCAGCCAG TGTGGGTCAC AGGCGAATGG GAGCCATGTA GCCAGACCTG   420

TGGGCGGACA GGCATGCAGG TGCGCTCCGT GCGCTGCATT CAGCCGCTAC ACGACAACAC   480

CACCCGCTCC GTGCACGCCA AGCACTGCAA TGACGCCCGG CCCGAGAGCC GCCGGGCCTG   540

CAGCCGCGAG CTCTGCCCTG GTCGTTGGCG AGCCGGGCCC TGGTCCCAGT GCTCAGTAAC   600

CTGTGGCAAC GGCACCCAGG AGCGGCCAGT GCTCTGCCGC ACCGCGGACG ACAGCTTCGG   660

CATCTGCCAG GAGGAGCGTC CTGAGACAGC GAGGACCTGC AGGCTTGGCC CCTGTCCCCG   720

AAACATCTCA GATCCCTCCA AGAAGAGCTA CGTAGTTCAG TGGCTGTCCC GCCCGGACCC   780

CGACTCGCCC ATCCGGAAGA TCTCGTCAAA GGGCCACTGC CAAGGCGACA AGTCAATATT   840

CTGTAGGATG GAAGTCTTGT CCCGCTATTG CTCCATCCCA GGCTACAACA AGCTGTGCTG   900
```

-continued

```
CAAGTCCTGT AACCTGTACA ACAACCTCAC CAACGTGGAG GGCAGGATAG AGCCACCGCC   960

TGGGAAGCAC AACGACATTG ACGTGTTCAT GCCTACCCTC CCAGTGCCCA CTGTAGCCAT  1020

GGAGGTGCGG CCATCACCAA GCACCCCCCT GGAGGTCCCT CTCAATGCCT CCAGCACCAA  1080

TGCCACAGAG GATCACCCAG AAACCAATGC CGTAGATGAA CCCTACAAAA TCCATGGCCT  1140

GGAAGATGAA GTCCAGCCAC CCAACCTAAT CCCTCGACGA CCGAGCCCCT ATGAAAAGAC  1200

CAGAAACCAA AGAATCCAAG AGCTCATTGA TGAGATGCGG AAGAAAGAGA TGCTCGGAAA  1260

GTTCTAATAA AATGGAAAGA TAGCATCCCT AGCATTTTTT TCTTGCTTAT AGAGATATTC  1320

CATGGGATAG CAAATCCTGT GTCATGGAGA TGAAGTCAAA ATTCCTGATT CCAAAAGGTT  1380

TTGAGAAAAC AAAGAGGGGG AATGACGTAA GAAAGATACG CATGAGCATG TGGTAAGCTA  1440

GGTTAGCACG TGTGCTTCCC AGCCCAGGAG CGACCAAATA CTGTGGTGGC GTCAGGTGTG  1500

CACTGGAGAG GAATATAGAG GCTGTATGGC CTCCCTCACT GAGGGCAGGG CAAGAGGGAT  1560

CACTCTACAA ACAAAAATAG GCCCCAAGTT GCTAAGCAGT GATTGGGAAC CTTCCTTTCC  1620

TTGGCGGAGA TGCATGACAT TCCCTACCGA TCCCCAGACA CAGCCTGTGG CAGTCTTAGG  1680

AGAAATGGTG ATTTACTGAA TAACTGACCC GTTGCCGAGA TGAGTACAAT GAAGTGGAGG  1740

TGATGAACTC AAATCGTCTT CCAGGGCCAG GCGGCTGACC GGGGTGAGCG TAGTGGCCCG  1800

CTGGGGACCA TGGCCGCCCT GACAGCCACA CCCACCTGGA GCTGACTTGG TTCTGGCTGT  1860

TGCTGCCACT GTGAAATCTG TATCTCTCTC CATCTCTGCT CTACTATCCC CGGCCTTGCC  1920

AGACAGTGTT CTTTTTCGGA AGAAGTCTAG ATTTTTGCAT GAAAAAAACT CAATCTTTAA  1980

AGGTCGACTC AGAACATTTT AAGGAGGCCT CCACTTGGTC TGATGCAGTC TTGCTAATTA  2040

AGAACTAAAA GGCTTCTGAC CTTCTTGGTG CTCATGCTGT ACGGCATCTG AATGTCTCGA  2100

CCGAGTCTGA GCCGTGCAGC TGTCCTCCAC CTGCGAAAGT AATGAGAATC CTATCACGGG  2160

ACATAAGGAT AGGTCTAAAC AGGGTCCATG CCAAGAAAAC AGTGGGGTGC TCTCCCAGGC  2220

CTCTCCCCTG TCCACTAACC CTGGCCTTGC CGGCTGCCTT CCAGGCTCTG GGGGAAGAGC  2280

TCCTGCATTC TTCCCTGGCC ACCTTGGCTC CAGGGCTCCC CAAGAGCCTC TTCCCTCCCC  2340

AAGTACCTGA GAAAGATGAG AGAGGCACGT GCTCTGCTGG GAAGGTCCAG TGAGCGGTTC  2400

AAGGGCCTGG AATCTCCCTA CGGCCAAGTC TAAGGGTTCT GGGATTCTGG             2450
```

(2) INFORMATION FOR SEQ ID NO:4:

(i) SEQUENCE CHARACTERISTICS:
(A) LENGTH: 1792 base pairs
(B) TYPE: nucleic acid
(C) STRANDEDNESS: single
(D) TOPOLOGY: linear (xi) SEQUENCE DESCRIPTION: SEQ ID NO:4:

```
GCTTTGTGGG CTTTGCTTGC TTGCTGGGAA TGGGCTTTCC CTGTCCCGCC TGCCCCACTT    60

GCTTTGTTTT CAGAAGCTCC AGAACCCAGC AGTGACTGCA AAATGTGGCT TGATGGGGGC   120

TTAGGGTGGG AGATGGGGAG AGCTACATTG TCTTTTGCTC CTTGAAAACT TTAATAGCTC   180

CTATTTTCCA GAGAATGGTG CTTTGTGAGC AACATGCGAG TAAGAGAGAA ATAGGAGGAA   240

GGGGGAGTAG GGGCGGATGG GAGAAGAGTG GCTCATTTTT ACCTCTCACT GCCTGACATT   300

TTGTGAACGT GAAGCTTAAA CTTTCTGGGC TTACAAGACC CAGGGGCACG TCAGCTCCTT   360

AGATGGGCTC AGCCTGACAC ATAATTCTTA AACCTTTCCT GTTTAAGAAA CTTCTAGAGG   420

CTGTGTACTC TCACCAATCC TCTTCGAGAA TTTGTTCATG TGTATTTCCC CATTATATGG   480
```

-continued

```
ATGAGGCTCA GGATAACAGC ATAGTGGCTA CCTTCTACTG AGTTTTGAGG TGCTAATAAG   540
TATGTTTGTC TGAGGCTGCA CATGTGGGTG GCTCTGTGTG TATGATCCAA GGGACAAAAT   600
GACGATGTAG AACCAGCAAG AACGGAATCT GGGCTGATGC TTCAGTCTCC ACCTGGGTGA   660
TGGTAGCCTC CCGCCCTCCA CCACCGCATC CCACACGTGC TGCGCACTGT CCCCGTGTCT   720
CCTGGAGAAC CAAACTGGAG AAAACCTTTC TGAGTATCTC TCATAGTACC CCTTCCTTAA   780
GAAGATGTGG TTTAGAGCAT GTGTGCAATC CTGCCTCTGT AATTAGGAAA CGGAGCCCGA   840
GGCTTTCCAT TGTTGGTTGA ACCCAGGACA GCTGGTGCTA TTCACAGGCT GAAGAACTGG   900
GCAGTTCTTA CTTGGGTCTG TCCTAGGATG TGGAGGAAGT TCAGGACTAA CGCTAGGCAG   960
AGAGTATGAC TCGGTTTACC CAGCCTAGGG GCCTCTGGAT GGGAACACTC CATTCCAAGA  1020
TCTCAGCAGA GCAGGGCTTC CTGGCTTGAG GCTGGAAGCC TTTGGGAAGA GGCCCAGCTG  1080
GGACATTACC TGGCACCTTC TTCCCGTTGA AGGGAGCAAG GTGCCCTCTG GGATGACAGC  1140
CAGACCCTTG TGCCATCCTC AATCTTGAGC CATATATCAA GAGTCCTCTA GAGCCGGATG  1200
GTCCTCAAAA GTCTGTCCAA GGAATGCCAA CGTTCACCGG GCTTGAGAAA CGACGCAAAT  1260
CTCTGAGCTG GGGACCACTT GGAGAACCGG CTTAGTAACA GTCCTGATCT TCGCAAGCCA  1320
GTTGTTGTGC ATCTGAGGGG CTCCTGGCGC CCAGAGGAGG CAGACAGATG CTTCTAGCTG  1380
AGTTTCTAAC CGCATGATGA GACTCAGACC TTCCGCTGCA TAGAAAATTG CAACAGTGTC  1440
CGGAGTCATT TTTCCTTAGT GGGCAGACTC GTGTTAGATT TGGGAACCCA GCTCTTGATT  1500
ACTCCTTTTG GAAAACCCAT GGAATTTCAT GTATAAGGCT TTCATTTGTA TTTTAAGGTT  1560
TTTTGTTTGT TTGAGTATAA CATGGTGCTC AATAGCAACA TCTTAGCAGA TGAAGCAGTT  1620
TATGATTCCA CTCCCTCCTG TATGACAGGT AGCCACTATA CTGAATCAAG GTGCTGAACT  1680
CAAATCACAA AATTCTGGCT TACCGATACA ACAACCAATA CATCTTTGTT TGTAATAAAA  1740
AATTTGACTC CTTACTTTTA TAACTTATTA AAGTTAAAAT GTCTGTGTTT TT          1792
```

(2) INFORMATION FOR SEQ ID NO:5:

(i) SEQUENCE CHARACTERISTICS:
(A) LENGTH: 1211 amino acids
(B) TYPE: amino acid
(C) STRANDEDNESS: single
(D) TOPOLOGY: linear (xi) SEQUENCE DESCRIPTION: SEQ ID NO:5:

```
Met Asp Pro Pro Ala Gly Ala Ala Arg Arg Leu Leu Cys Pro Ala Leu
 1               5                  10                  15

Leu Leu Leu Leu Leu Leu Leu Pro Pro Pro Leu Leu Pro Pro Pro Pro
            20                  25                  30

Pro Pro Ala Asn Ala Arg Leu Ala Ala Ala Ala Asp Pro Pro Gly Gly
        35                  40                  45

Pro Leu Gly His Gly Ala Glu Arg Ile Leu Ala Val Pro Val Arg Thr
    50                  55                  60

Asp Ala Gln Gly Arg Leu Val Ser His Val Val Ser Ala Ala Thr Ser
65                  70                  75                  80

Arg Ala Gly Val Arg Ala Arg Arg Ala Ala Pro Val Arg Thr Pro Ser
                85                  90                  95

Phe Pro Gly Gly Asn Glu Glu Glu Pro Gly Ser His Leu Phe Tyr Asn
            100                 105                 110

Val Thr Val Phe Gly Arg Asp Leu His Leu Arg Leu Arg Pro Asn Ala
        115                 120                 125
```

-continued

```
Arg Leu Val Ala Pro Gly Ala Thr Met Glu Trp Gln Gly Glu Lys Gly
    130                 135                 140

Thr Thr Arg Val Glu Pro Leu Leu Gly Ser Cys Leu Tyr Val Gly Asp
145                 150                 155                 160

Val Ala Gly Leu Ala Glu Ala Ser Ser Val Ala Leu Ser Asn Cys Asp
                165                 170                 175

Gly Leu Ala Gly Leu Ile Arg Met Glu Glu Glu Glu Phe Phe Ile Glu
            180                 185                 190

Pro Leu Glu Lys Gly Leu Ala Ala Gln Glu Ala Glu Gln Gly Arg Val
        195                 200                 205

His Val Val Tyr Arg Arg Pro Pro Thr Ser Pro Pro Leu Gly Gly Pro
    210                 215                 220

Gln Ala Leu Asp Thr Gly Ala Ser Leu Asp Ser Leu Asp Ser Leu Ser
225                 230                 235                 240

Arg Ala Leu Gly Val Leu Glu Glu His Ala Asn Ser Ser Arg Arg Arg
                245                 250                 255

Ala Arg Arg His Ala Ala Asp Asp Asp Tyr Asn Glu Ile Val Leu Leu
            260                 265                 270

Gly Val Asp Asp Ser Val Val Gln Phe His Gly Lys Glu His Val Gln
        275                 280                 285

Lys Tyr Leu Leu Thr Leu Met Asn Ile Val Asn Glu Ile Tyr His Asp
    290                 295                 300

Glu Ser Leu Gly Ala His Ile Asn Val Val Leu Val Arg Ile Ile Leu
305                 310                 315                 320

Leu Ser Tyr Gly Lys Ser Met Ser Leu Ile Glu Ile Gly Asn Pro Ser
                325                 330                 335

Gln Ser Leu Glu Asn Val Cys Arg Trp Ala Tyr Leu Gln Gln Lys Pro
            340                 345                 350

Asp Thr Gly His Asp Glu Tyr His Asp His Ala Ile Phe Leu Thr Arg
        355                 360                 365

Gln Asp Phe Gly Pro Ser Gly Met Gln Gly Tyr Ala Pro Val Thr Gly
    370                 375                 380

Met Cys His Pro Val Arg Ser Cys Thr Leu Asn His Glu Asp Gly Phe
385                 390                 395                 400

Ser Ser Ala Phe Val Val Ala His Glu Thr Gly His Val Leu Gly Met
                405                 410                 415

Glu His Asp Gly Gln Gly Asn Arg Cys Gly Asp Glu Val Arg Leu Gly
            420                 425                 430

Ser Ile Met Ala Pro Leu Val Gln Ala Ala Phe His Arg Phe His Trp
        435                 440                 445

Ser Arg Cys Ser Gln Gln Glu Leu Ser Arg Tyr Leu His Ser Tyr Asp
    450                 455                 460

Cys Leu Leu Asp Asp Pro Phe Ala His Asp Trp Pro Ala Leu Pro Gln
465                 470                 475                 480

Leu Pro Gly Leu His Tyr Ser Met Asn Glu Gln Cys Arg Phe Asp Phe
                485                 490                 495

Gly Leu Gly Tyr Met Met Cys Thr Ala Phe Arg Thr Phe Asp Pro Cys
            500                 505                 510

Lys Gln Leu Trp Cys Ser His Pro Asp Asn Pro Tyr Phe Cys Lys Thr
        515                 520                 525

Lys Lys Gly Pro Pro Leu Asp Gly Thr Met Cys Ala Pro Gly Lys His
    530                 535                 540
```

-continued

```
Cys Phe Lys Gly His Cys Ile Trp Leu Thr Pro Asp Ile Leu Lys Arg
545                 550                 555                 560

Asp Gly Ser Trp Gly Ala Trp Ser Pro Phe Gly Ser Cys Ser Arg Thr
                565                 570                 575

Cys Gly Thr Gly Val Lys Phe Arg Thr Arg Gln Cys Asp Asn Pro His
            580                 585                 590

Pro Ala Asn Gly Gly Arg Thr Cys Ser Gly Leu Ala Tyr Asp Phe Gln
        595                 600                 605

Leu Cys Ser Arg Gln Asp Cys Pro Asp Ser Leu Ala Asp Phe Arg Glu
    610                 615                 620

Glu Gln Cys Arg Gln Trp Asp Leu Tyr Phe Glu His Gly Asp Ala Gln
625                 630                 635                 640

His His Trp Leu Pro His Glu His Arg Asp Ala Lys Glu Arg Cys His
                645                 650                 655

Leu Tyr Cys Glu Ser Arg Glu Thr Gly Glu Val Val Ser Met Lys Arg
            660                 665                 670

Met Val His Asp Gly Thr Arg Cys Ser Tyr Lys Asp Ala Phe Ser Leu
        675                 680                 685

Gln Val Arg Gly Asp Cys Arg Lys Val Gly Cys Asp Gly Val Ile Gly
    690                 695                 700

Ser Ser Lys Gln Glu Asp Lys Cys Gly Val Cys Gly Gly Asp Asn Ser
705                 710                 715                 720

His Cys Lys Val Val Lys Gly Thr Phe Thr Arg Ser Pro Lys Lys His
                725                 730                 735

Gly Tyr Ile Lys Met Phe Glu Ile Pro Ala Gly Ala Arg His Leu Leu
            740                 745                 750

Ile Gln Glu Val Asp Ala Thr Ser His His Leu Ala Val Lys Asn Leu
        755                 760                 765

Glu Thr Gly Lys Phe Ile Leu Asn Glu Glu Asn Asp Val Asp Ala Ser
    770                 775                 780

Ser Lys Thr Phe Ile Ala Met Gly Val Glu Trp Glu Tyr Arg Asp Glu
785                 790                 795                 800

Asp Gly Arg Glu Thr Leu Gln Thr Met Gly Pro Leu His Gly Thr Ile
                805                 810                 815

Thr Val Leu Val Ile Pro Val Gly Asp Thr Arg Val Ser Leu Thr Tyr
            820                 825                 830

Lys Tyr Met Ile His Glu Asp Ser Leu Asn Val Asp Asp Asn Asn Val
        835                 840                 845

Leu Glu Glu Asp Ser Val Val Tyr Glu Trp Ala Leu Lys Lys Trp Ser
    850                 855                 860

Pro Cys Ser Lys Pro Cys Gly Gly Gly Ser Gln Phe Thr Lys Tyr Gly
865                 870                 875                 880

Cys Arg Arg Arg Leu Asp His Lys Met Val His Arg Gly Phe Cys Ala
                885                 890                 895

Ala Leu Ser Lys Pro Lys Ala Ile Arg Arg Ala Cys Asn Pro Asp Glu
            900                 905                 910

Cys Ser Gln Pro Val Trp Val Thr Gly Glu Trp Glu Pro Cys Ser Gln
        915                 920                 925

Thr Cys Gly Arg Thr Gly Met Gln Val Arg Ser Val Arg Cys Ile Gln
    930                 935                 940

Pro Leu His Asp Asn Thr Thr Arg Ser Val His Ala Lys His Cys Asn
945                 950                 955                 960

Asp Ala Arg Pro Glu Ser Arg Arg Ala Cys Ser Arg Glu Leu Cys Pro
```

-continued

```
                965                 970                 975

Gly Arg Trp Arg Ala Gly Pro Trp Ser Gln Cys Ser Val Thr Cys Gly
            980                 985                 990

Asn Gly Thr Gln Glu Arg Pro Val Leu Cys Arg Thr Ala Asp Asp Ser
        995                 1000                1005

Phe Gly Ile Cys Gln Glu Glu Arg Pro Glu Thr Ala Arg Thr Cys Arg
    1010                1015                1020

Leu Gly Pro Cys Pro Arg Asn Ile Ser Asp Pro Ser Lys Lys Ser Tyr
1025                1030                1035                104

Val Val Gln Trp Leu Ser Arg Pro Asp Pro Asp Ser Pro Ile Arg Lys
                1045                1050                1055

Ile Ser Ser Lys Gly His Cys Gln Gly Asp Lys Ser Ile Phe Cys Arg
            1060                1065                1070

Met Glu Val Leu Ser Arg Tyr Cys Ser Ile Pro Gly Tyr Asn Lys Leu
        1075                1080                1085

Cys Cys Lys Ser Cys Asn Leu Tyr Asn Asn Leu Thr Asn Val Glu Gly
    1090                1095                1100

Arg Ile Glu Pro Pro Pro Gly Lys His Asn Asp Ile Asp Val Phe Met
1105                1110                1115                112

Pro Thr Leu Pro Val Pro Thr Val Ala Met Glu Val Arg Pro Ser Pro
                1125                1130                1135

Ser Thr Pro Leu Glu Val Pro Leu Asn Ala Ser Ser Thr Asn Ala Thr
            1140                1145                1150

Glu Asp His Pro Glu Thr Asn Ala Val Asp Glu Pro Tyr Lys Ile His
        1155                1160                1165

Gly Leu Glu Asp Glu Val Gln Pro Pro Asn Leu Ile Pro Arg Arg Pro
    1170                1175                1180

Ser Pro Tyr Glu Lys Thr Arg Asn Gln Arg Ile Gln Glu Leu Ile Asp
1185                1190                1195                120

Glu Met Arg Lys Lys Glu Met Leu Gly Lys Phe
                1205                1210
```

(2) INFORMATION FOR SEQ ID NO:6:

(i) SEQUENCE CHARACTERISTICS:
(A) LENGTH: 2023 base pairs
(B) TYPE: nucleic acid
(C) STRANDEDNESS: single
(D) TOPOLOGY: linear (xi) SEQUENCE DESCRIPTION: SEQ ID NO:6:

```
GCCCCAGATG TGGGCTGGGC GGCTCGCGGG GAACTTTCGC GCCGGCTGCG AGTGCGGGGC    60

CCCGGCTGCA GTCCGGCTGC CATGGATCCG CCGGCGGGAG CCGCTCGCCG CCTGCTCTGC   120

CCCGCGCTGC TGCTGCTGCT GCTGCTGCTG CCGCCGCCGC TCCTGCCGCC GCCGCCGCCG   180

CCCGCGAACG CCAGGCTCGC CGCCGCCGCC GACCCCCCAG GCGGGCCCCT GGGGCACGGA   240

GCGGAGCGCA TCCTGGCGGT GCCCGTGCGC ACTGACGCCC AGGGCCGCTT GGTGTCCCAC   300

GTGGTGTCGG CAGCTACGTC CAGAGCAGGG GTACGAGCCC GCAGGGCCGC CCCGGTCCGG   360

ACCCCGAGCT TCCCCGGAGG CAACGAGGAG GAGCCTGGCA GTCACCTCTT CTACAATGTC   420

ACGGTCTTTG GCCGAGACCT GCACCTGCGG CTGCGGCCCA ACGCCCGCCT CGTGGCGCCC   480

GGGGCCACTA TGGAGTGGCA GGGCGAGAAG GGCACCACCC GCGTGGAGCC CCTGCTCGGG   540

AGCTGTCTCT ACGTCGGAGA CGTGGCCGGC CTAGCCGAAG CCTCCTCTGT GGCGCTCAGC   600

AACTGCGATG GGCTGGCTGG TCTGATCCGG ATGGAGGAGG AGGAGTTCTT CATCGAACCC   660
```

-continued

```
TTGGAGAAGG GGCTGGCGGC GCAGGAGGCT GAGCAAGGCC GTGTGCATGT GGTGTATCGC   720

CGGCCACCCA CGTCCCCTCC TCTCGGGGGG CCACAGGCCC TGGACACAGG GGCCTCCCTG   780

GACAGCCTGG ACAGCCTCAG CCGCGCCCTG GGCGTCCTAG AGGAGCACGC CAACAGCTCG   840

AGGCGGAGGG CACGCAGGCA TGCTGCAGAC GATGACTACA ACATCGAGGT CCTGCTGGGC   900

GTGGATGACT CTGTGGTGCA GTTCCACGGG AAGGAGCACG TACAGAAGTA CCTGCTGACA   960

CTCATGAACA TTGTCAATGA AATCTACCAT GACGAGTCCT TGGGTGCCCA CATCAACGTG  1020

GTCCTGGTGC GGATCATCCT CCTGAGCTAT GGAAAGTCCA TGAGCCTCAT CGAGATCGGG  1080

AACCCCTCTC AGAGCCTGGA GAATGTCTGC CGCTGGGCCT ACCTCCAGCA GAAGCCAGAC  1140

ACGGGCCACG ATGAATACCA CGATCACGCC ATCTTCCTCA CACGGCAGGA CTTTGGGCCT  1200

TCCGGCATGC AAGGCTATGC TCCTGTCACC GGCATGTGCC ATCCGGTCCG CAGCTGCACC  1260

CTGAACCATG AGGACGGCTT CTCCTCAGCG TTTGTGGTGG CCCATGAGAC TGGCCACGTG  1320

CTGGGCATGG AGCACGACGG GCAGGGCAAC CGCTGTGGCG ACGAGGTGCG GCTGGGCAGC  1380

ATCATGGCGC CCCTGGTGCA GGCCGCCTTC CACCGCTTCC ACTGGTCCCG CTGCAGCCAG  1440

CAGGAGCTGA GCCGCTACCT GCACTCCTAT GACTGCCTGC TGGATGACCC CTTCGCCCAC  1500

GACTGGCCGG CGCTGCCCCA GCTCCCGGGA CTGCACTACT CCATGAACGA GCAATGCCGC  1560

TTTGACTTCG GCCTGGGCTA CATGATGTGC ACGGCGTTCC GGACCTTTGA CCCCTGCAAG  1620

CAGCTGTGGT GCAGCCATCC TGACAACCCC TACTTTTGCA AGACCAAGAA GGGGCCCCCC  1680

TTGGACGGGA CTATGTGTGC ACCTGGCAAG TTCAGGCCGG GCGCGGTGGC TCATGCCTGT  1740

TATCCCAGCA CTTTGGGAGG CCAAGGTAGG TGGATCGCCT GAGGTCAGAA GTTCAAGACA  1800

AGTGTGGTTA ACATGGCAAA ATCCCGTCTC TACTAAAAAT ACAAAAATTA GCTGGGCGCG  1860

GTGGTGGGTG CCTGTAATCC CAGCTACTCC GGAGGCTGAG GCATGAAAAT CGTTTGAGCC  1920

CAGGAGGCGG AGGTTGCGGT GAGCCAAGAT CGCGTCGCTG CTTCCAGTCT GGATCACACA  1980

GCAAGACCCT GTCTCAAAAA ATAAAAATAA AAGTGAAGTG CAC                    2023
```

(2) INFORMATION FOR SEQ ID NO:7:

(i) SEQUENCE CHARACTERISTICS:
(A) LENGTH: 566 amino acids
(B) TYPE: amino acid
(C) STRANDEDNESS: single
(D) TOPOLOGY: linear (xi) SEQUENCE DESCRIPTION: SEQ ID NO:7:

```
Met Asp Pro Pro Ala Gly Ala Ala Arg Arg Leu Leu Cys Pro Ala Leu
 1               5                  10                  15

Leu Leu Leu Leu Leu Leu Leu Pro Pro Pro Leu Leu Pro Pro Pro Pro
            20                  25                  30

Pro Pro Ala Asn Ala Arg Leu Ala Ala Ala Ala Asp Pro Pro Gly Gly
        35                  40                  45

Pro Leu Gly His Gly Ala Glu Arg Ile Leu Ala Val Pro Val Arg Thr
    50                  55                  60

Asp Ala Gln Gly Arg Leu Val Ser His Val Val Ser Ala Ala Thr Ser
65                  70                  75                  80

Arg Ala Gly Val Arg Ala Arg Arg Ala Ala Pro Val Arg Thr Pro Ser
                85                  90                  95

Phe Pro Gly Gly Asn Glu Glu Glu Pro Gly Ser His Leu Phe Tyr Asn
            100                 105                 110
```

-continued

```
Val Thr Val Phe Gly Arg Asp Leu His Leu Arg Leu Arg Pro Asn Ala
        115                 120                 125

Arg Leu Val Ala Pro Gly Ala Thr Met Glu Trp Gln Gly Glu Lys Gly
    130                 135                 140

Thr Thr Arg Val Glu Pro Leu Leu Gly Ser Cys Leu Tyr Val Gly Asp
145                 150                 155                 160

Val Ala Gly Leu Ala Glu Ala Ser Ser Val Ala Leu Ser Asn Cys Asp
                165                 170                 175

Gly Leu Ala Gly Leu Ile Arg Met Glu Glu Glu Glu Phe Phe Ile Glu
            180                 185                 190

Pro Leu Glu Lys Gly Leu Ala Ala Gln Glu Ala Glu Gln Gly Arg Val
        195                 200                 205

His Val Val Tyr Arg Arg Pro Pro Thr Ser Pro Pro Leu Gly Gly Pro
    210                 215                 220

Gln Ala Leu Asp Thr Gly Ala Ser Leu Asp Ser Leu Asp Ser Leu Ser
225                 230                 235                 240

Arg Ala Leu Gly Val Leu Glu Glu His Ala Asn Ser Ser Arg Arg Arg
                245                 250                 255

Ala Arg Arg His Ala Ala Asp Asp Asp Tyr Asn Ile Glu Val Leu Leu
            260                 265                 270

Gly Val Asp Asp Ser Val Val Gln Phe His Gly Lys Glu His Val Gln
        275                 280                 285

Lys Tyr Leu Leu Thr Leu Met Asn Ile Val Asn Glu Ile Tyr His Asp
    290                 295                 300

Glu Ser Leu Gly Ala His Ile Asn Val Val Leu Val Arg Ile Ile Leu
305                 310                 315                 320

Leu Ser Tyr Gly Lys Ser Met Ser Leu Ile Glu Ile Gly Asn Pro Ser
                325                 330                 335

Gln Ser Leu Glu Asn Val Cys Arg Trp Ala Tyr Leu Gln Gln Lys Pro
            340                 345                 350

Asp Thr Gly His Asp Glu Tyr His Asp His Ala Ile Phe Leu Thr Arg
        355                 360                 365

Gln Asp Phe Gly Pro Ser Gly Met Gln Gly Tyr Ala Pro Val Thr Gly
    370                 375                 380

Met Cys His Pro Val Arg Ser Cys Thr Leu Asn His Glu Asp Gly Phe
385                 390                 395                 400

Ser Ser Ala Phe Val Val Ala His Glu Thr Gly His Val Leu Gly Met
                405                 410                 415

Glu His Asp Gly Gln Gly Asn Arg Cys Gly Asp Glu Val Arg Leu Gly
            420                 425                 430

Ser Ile Met Ala Pro Leu Val Gln Ala Ala Phe His Arg Phe His Trp
        435                 440                 445

Ser Arg Cys Ser Gln Gln Glu Leu Ser Arg Tyr Leu His Ser Tyr Asp
    450                 455                 460

Cys Leu Leu Asp Asp Pro Phe Ala His Asp Trp Pro Ala Leu Pro Gln
465                 470                 475                 480

Leu Pro Gly Leu His Tyr Ser Met Asn Glu Gln Cys Arg Phe Asp Phe
                485                 490                 495

Gly Leu Gly Tyr Met Met Cys Thr Ala Phe Arg Thr Phe Asp Pro Cys
            500                 505                 510

Lys Gln Leu Trp Cys Ser His Pro Asp Asn Pro Tyr Phe Cys Lys Thr
        515                 520                 525

Lys Lys Gly Pro Pro Leu Asp Gly Thr Met Cys Ala Pro Gly Lys Phe
```

-continued

```
    530                 535                 540

Arg Pro Gly Ala Val Ala Gly Ala Cys Tyr Pro Ser Thr Leu Gly Gly
545                 550                 555                 560

Gln Gly Arg Trp Ile Ala
                565
```

(2) INFORMATION FOR SEQ ID NO:8:

(i) SEQUENCE CHARACTERISTICS:
(A) LENGTH: 4580 base pairs
(B) TYPE: nucleic acid
(C) STRANDEDNESS: single
(D) TOPOLOGY: linear (xi) SEQUENCE DESCRIPTION: SEQ ID NO:8:

```
TCGAGCCCTC CTCCGCCCCG CGCCCTGCGG TGCTGCAGCT GCGGGCGGCT CCAGCTGCCC    60

CAGATGTGGG CTGGGCGGCG CGCGGGGAAC TTTCGCGCCG GCTGCGAGTG CGGGGCCCCG   120

GCTGTGGTCC GGCTGCCATG GATCCGCCGG CGGGAGCCGC CGGCCGCCTG CTCTGCCCCG   180

CGCTGTTGCT GCTCCTGCTG CTGCCGCTGC CCGCGGACGC CCGGCTCGCC GCCGCTGCCG   240

CCGACCCCCC AGGCGGGCCC CAGGGGCACG GAGCCGAGCG CATCCTGGCG GTGCCGGTGC   300

GCACTGACGC CCAGGGCCGC TTGGTGTCCC ACGTGGTGTC GGCGGCGACG GCCCCAGCTG   360

GGGTGCGGAC CCGCAGGGCC GCCCCTGCCC AGATCCCGGG GCTCTCTGGA GGCAGCGAGG   420

AGGACCCCGG TGGCCGCCTC TTCTACAATG TTACGGTGTT TGGCCGAGAC CTGCACCTGC   480

GGCTGCGGCC CAACGCCCGC CTCGTGGCGC CTGGGGCCAC GGTGGAGTGG CAGGGAGAAT   540

CGGGTGCCAC CCGCGTGGAG CCCCTGCTTG GGACCTGCCT CTACGTCGGA GACGTCGCGG   600

GCCTGGCTGA ATCCTCTTCC GTGGCGCTCA GCAACTGCGA TGGGCTGGCT GGCCTGATCC   660

GTATGGAAGA GGAGGAATTC TTTATTGAGC CCCTGGAGAA AGGTCTGGCG GCGAAGGAGG   720

CCGAACAGGG CCGTGTACAC GTGGTGTATC ATCGACCGAC CACCTCCAGA CCCCCTCCTC   780

TGGGGGGGCC ACAGGCCCTG GACACAGGGA TCTCCGCAGA CAGCCTGGAC AGCCTCAGCC   840

GTGCTCTGGG TGTTCTGGAG GAGCGAGTCA ACAGCTCCAG GCGGAGGATG CGCAGGCATG   900

CTGCCGACGA CGACTACAAC ATCGAGGTCC TGCTTGGGGT GGACGACTCT GTGGTCCAGT   960

TCCACGGGAC GGAGCACGTG CAGAAGTACC TGCTCACCCT CATGAACATT GTCAACGAAA  1020

TCTATCACGA TGAGTCCTTG GGGGCCCACA TCAATGTCGT CCTGGTGCGG ATAATCCTGC  1080

TGAGCTACGG GAAGTCCATG AGTCTCATTG AGATTGGGAA CCCCTCTCAA AGTCTGGAGA  1140

ATGTTTGCCG CTGGGCCTAC CTCCAGCAGA AGCCAGACAC TGATCACGAC GAGTACCACG  1200

ATCACGCCAT ATTCCTCACA CGGCAGGACT TCGGGCCCTC GGGCATGCAA GGCTATGCTC  1260

CTGTCACTGG GATGTGCCAC CCCGTCCGCA GCTGCACGCT GAACCACGAG GACGGCTTCT  1320

CCTCTGCGTT CGTGGTGGCC CACGAGACTG GCCATGTGCT GGGCATGGAG CATGATGGGC  1380

AGGGCAACCG CTGCGGTGAC GAGGTGCGGC TGGGCAGCAT CATGGCGCCC CTGGTGCAGG  1440

CAGCCTTCCA TCGCTTCCAC TGGTCCCGCT GCAGCCAGCA GGAGCTGAGC CGCTACCTGC  1500

ACTCCTATGA CTGCCTGCGG GATGACCCCT TCACCCACGA CTGGCCGGCG CTGCCCCAGC  1560

TCCCCGGGCT GCACTACTCC ATGAACGAGC AGTGCCGTTT CGACTTTGGC CTTGGTTACA  1620

TGATGTGTAC CGCGTTCCGG ACCTTCGACC CGTGCAAACA GCTGTGGTGC AGCCACCCTG  1680

ACAACCCCTA CTTTTGCAAG ACAAAGAAGG GGCCACCCCT GGATGGGACC ATGTGTGCGC  1740

CTGGCAAGCA CTGCTTTAAA GGACACTGCA TCTGGCTGAC ACCTGACATT CTCAAACGAG  1800
```

-continued

```
ATGGCAACTG GGGTGCCTGG AGTCCCTTCG GCTCCTGCTC GCGTACCTGC GGCACAGGTG  1860
TGAAGTTCAG GACCCGTCAG TGCGACAACC CACACCCAGC CAATGGGGGC CGCACATGCT  1920
CGGGCCTCGC CTACGATTTC CAGCTCTGCA ACTCGCAGGA CTGCCCTGAC GCGCTGGCCG  1980
ACTTCCGCGA GGAGCAGTGC CGGCAGTGGG ACCTGTACTT CGAGCATGGT GACGCTCAAC  2040
ACCACTGGCT GCCCCACGAG CACCGGGACG CCAAGGAGCG GTGTCATCTC TACTGTGAGT  2100
CCAAGGAGAC CGGGGAGGTG GTGTCCATGA AGCGTATGGT GCATGACGGG ACACGCTGTT  2160
CCTACAAGGA CGCCTTCAGC CTCTGCGTGC GTGGGGACTG CAGGAAGGTG GGCTGTGACG  2220
GGGTGATCGG CTCCAGCAAG CAGGAGGACA AGTGTGGTGT GTGCGGAGGG GACAACTCCC  2280
ACTGCAAGGT GGTCAAGGGC ACGTTCTCGC GCTCGCCCAA GAAGCTTGGT TACATCAAGA  2340
TGTTTGAGAT CCCGGCAGGA GCCAGACACC TGCTAATCCA GGAAGCAGAC ACCACCAGCC  2400
ATCACCTGGC CGTCAAAAAC CTGGAGACAG GCAAGTTCAT TTTAAATGAG GAGAATGACG  2460
TGGATCCCAA CTCCAAGACC TTCATCGCCA TGGGCGTGGA GTGGGAGTAC CGGGATGAGG  2520
ACGGCCGGGA GACGCTGCAG ACCATGGGCC CCCTCCACGG CACCATCACT GTGCTGGTCA  2580
TCCCAGAGGG GGACGCCCGC ATCTCACTGA CCTACAAGTA CATGATCCAT GAGGACTCGC  2640
TCAATGTGGA TGACAACAAC GTCCTGGAAG ACGACTCTGT GGGCTATGAG TGGGCCCTGA  2700
AGAAGTGGTC GCCCTGCTCC AAGCCCTGCG GTGGAGGGTC CCAATTCACC AAGTATGGCT  2760
GCCGCCGGAG GCTGGACCAC AAGATGGTGC ACCGAGGCTT CTGCGACTCC GTCTCAAAGC  2820
CCAAAGCCAT CCGCCGGACC TGCAACCCAC AGGAGTGCTC CCAGCCCGTG TGGGTCACGG  2880
GTGAGTGGGA GCCGTGCAGC CGGAGCTGTG GGCGGACAGG CATGCAGGTT CGCTCTGTGC  2940
GCTGTGTTCA GCCTCTGCAC AACAACACCA CCCGCTCCGT GCACACCAAG CACTGCAATG  3000
ACGCTCGACC CGAGGGCCGC CGGGCCTGCA ACCGCGAGCT GTGCCCTGGC CGGTGGCGGG  3060
CTGGATCCTG GTCCCAGTGC TCAGTAACCT GTGGAAACGG CACCCAGGAA CGGCCAGTGC  3120
TCTGCCGAAC TGCGGACGAC AGTTTCGGGG TGTGCCGGGA GGAGCGGCCT GAGACGGCAA  3180
GGATCTGCAG GCTTGGCCCC TGTCCCCGAA ACACCTCTGA CCCCTCCAAG AAGAGCTACG  3240
TGGTCCAGTG GCTATCCCGA CCGGACCCCA ACTCGCCAGT CCAGGAGACC TCGTCAAAGG  3300
GCCGCTGCCA AGGTGACAAG TCAGTGTTCT GTAGGATGGA AGTCTTGTCT CGTTATTGCT  3360
CCATCCCAGG CTACAATAAG CTGTGCTGCA AGTCCTGTAA CCCGCACGAC AACCTCACTG  3420
ATGTGGACGA CAGGGCAGAG CCACCCTCTG GGAAGCACAA TGACATTGAA GAGCTCATGC  3480
CCACCCTTTC AGTGCCCACT CTAGTCATGG AGGTGCAGCC TCCGCCAGGC ATACCCCTGG  3540
AGGTGCCTCT CAATACTTCC AGCACCAATG CCACCGAGGA CCATCCAGAA ACCAATGCTG  3600
TGGATGTGCC CTACAAAATC CCTGGCCTGG AAGATGAAGT CCAGCCACCC AACCTGATCC  3660
CTCGACGACC GAGCCCATAT GAAAAGACCA GAAACCAAAG AATCCAAGAG CTCATTGATG  3720
AGATGAGGAA GAAAGAGATG CTCGGAAAGT TCTAATAAAA TGGAAAGATA GCATCAATAG  3780
CTTTTTTTTG CTTGCTTATA GAGATATTCC ATGGCAACTC CTGTGTTGTG GAGATGAAGT  3840
CAGATTCCTG ACTCCAAAAG GTTTTGAGGA AACAAAGAAG GAGAATAATG TAAATATATA  3900
GCTATATTTA CATTATACAC ACACACACAC ACACACATAG TTGTAAGCAT GTGGCAACTA  3960
GGTTGGTACC TATGTTTCCT AGTCCTGGAA TGTTCTAAGT CCTGCACTGG GGTTGGGTGT  4020
GGGGTAGAGA GGAATATGGA GGCTCTACAC CTCCCATCAA TGAGGGACAG CAGGAGGGAG  4080
AGAAAAAACC TTTGCCCCAA GTTTCTGAGC AGTGATTGCG AATCTTTTCC TTGCGGTGAC  4140
AACCCTGCTG GAGACGCAGG ACAGTTCCTA CCAATCTCCA GGTTGAGGTA CAAGACCCAT  4200
```

```
GGGGCTCTTA CAAGAAACAG TGATTTATTT ACTAAGTGAC CAGTCATTAA GACGAATGCA  4260
GTGAAGTGGA GGTCATGAAT TCCAGCAAAC TCCAGGACGA GGTGGTGAGG CAGGTGGCGT  4320
GGATGAGTGT GGTCACCAGC TGGCACTCCC AGGCTCTCAC ACCTCTCTCT TCTTCACTAA  4380
CCTTGGCCTT GCTTGTCACC TCTGGCCAGC CTGGCCTCAG GCCTGGGGCT CCCCAGAGAC  4440
ACTCTCTGCT TCCTCAAGTC ACTGGAAGGA TGAAGGAGGC ATGCACTCTG CTGGAAAATC  4500
CAGTGAGTGG TCAGGGCTCA TTTTTCTGTG TGTGAACATG TAGCTTAAAC TTCCCGAAAT  4560
TACAGGACCC AAACACCAAG                                              4580
```

(2) INFORMATION FOR SEQ ID NO:9:

(i) SEQUENCE CHARACTERISTICS:
(A) LENGTH: 2450 base pairs
(B) TYPE: nucleic acid
(C) STRANDEDNESS: single
(D) TOPOLOGY: linear (xi) SEQUENCE DESCRIPTION: SEQ ID NO:9:

```
TCGAGCCCTC CTCCGCCCCG CGCCCTGCGG TGCTGCAGCT GCGGGCGGCT CCAGCTGCCC    60
CAGATGTGGG CTGGGCGGCG CGCGGGGAAC TTTCGCGCCG GCTGCGAGTG CGGGGCCCCG   120
GCTGTGGTCC GGCTGCCATG GATCCGCCGG CGGGAGCCGC CGGCCGCCTG CTCTGCCCCG   180
CGCTGTTGCT GCTCCTGCTG CTGCCGCTGC CCGCGGACGC CCGGCTCGCC GCCGCTGCCG   240
CCGACCCCCC AGGCGGGCCC CAGGGGCACG GAGCCGAGCG CATCCTGGCG GTGCCGGTGC   300
GCACTGACGC CCAGGGCCGC TTGGTGTCCC ACGTGGTGTC GGCGGCGACG GCCCCAGCTG   360
GGGTGCGGAC CCGCAGGGCC GCCCCTGCCC AGATCCCGGG GCTCTCTGGA GGCAGCGAGG   420
AGGACCCCGG TGGCCGCCTC TTCTACAATG TTACGGTGTT TGGCCGAGAC CTGCACCTGC   480
GGCTGCGGCC CAACGCCCGC CTCGTGGCGC CTGGGGCCAC GGTGGAGTGG CAGGGAGAAT   540
CGGGTGCCAC CCGCGTGGAG CCCCTGCTTG GGACCTGCCT CTACGTCGGA GACGTCGCGG   600
GCCTGGCTGA ATCCTCTTCC GTGGCGCTCA GCAACTGCGA TGGGCTGGCT GGCCTGATCC   660
GTATGGAAGA GGAGGAATTC TTTATTGAGC CCCTGGAGAA AGGTCTGGCG GCGAAGGAGG   720
CCGAACAGGG CCGTGTACAC GTGGTGTATC ATCGACCGAC CACCTCCAGA CCCCCTCCTC   780
TGGGGGGGCC ACAGGCCCTG GACACAGGGA TCTCCGCAGA CAGCCTGGAC AGCCTCAGCC   840
GTGCTCTGGG TGTTCTGGAG GAGCGAGTCA ACAGCTCCAG GCGGAGGATG CGCAGGCATG   900
CTGCCGACGA CGACTACAAC ATCGAGGTCC TGCTTGGGGT GGACGACTCT GTGGTCCAGT   960
TCCACGGGAC GGAGCACGTG CAGAAGTACC TGCTCACCCT CATGAACATT GTCAACGAAA  1020
TCTATCACGA TGAGTCCTTG GGGGCCCACA TCAATGTCGT CCTGGTGCGG ATAATCCTGC  1080
TGAGCTACGG GAAGTCCATG AGTCTCATTG AGATTGGGAA CCCCTCTCAA AGTCTGGAGA  1140
ATGTTTGCCG CTGGGCCTAC CTCCAGCAGA AGCCAGACAC TGATCACGAC GAGTACCACG  1200
ATCACGCCAT ATTCCTCACA CGGCAGGACT TCGGGCCCTC GGGCATGCAA GGCTATGCTC  1260
CTGTCACTGG GATGTGCCAC CCCGTCCGCA GCTGCACGCT GAACCACGAG GACGGCTTCT  1320
CCTCTGCGTT CGTGGTGGCC CACGAGACTG GCCATGTGCT GGGCATGGAG CATGATGGGC  1380
AGGGCAACCG CTGCGGTGAC GAGGTGCGGC TGGGCAGCAT CATGGCGCCC CTGGTGCAGG  1440
CAGCCTTCCA TCGCTTCCAC TGGTCCCGCT GCAGCCAGCA GGAGCTGAGC CGCTACCTGC  1500
ACTCCTATGA CTGCCTGCGG GATGACCCCT TCACCCACGA CTGGCCGGCG CTGCCCCAGC  1560
TCCCCGGGCT GCACTACTCC ATGAACGAGC AGTGCCGTTT CGACTTTGGC CTTGGTTACA  1620
```

-continued

TGATGTGTAC CGCGTTCCGG ACCTTCGACC CGTGCAAACA GCTGTGGTGC AGCCACCCTG 1680

ACAACCCCTA CTTTTGCAAG ACAAAGAAGG GGCCACCCCT GGATGGGACC ATGTGTGCGC 1740

CTGGCAAGCA CTGCTTTAAA GGACACTGCA TCTGGCTGAC ACCTGACATT CTCAAACGAG 1800

ATGGCAACTG GGGTGCCTGG AGTCCCTTCG GCTCCTGCTC GCGTACCTGC GGCACAGGTG 1860

TGAAGTTCAG GACCCGTCAG TGCGACAACC CACACCCAGC CAATGGGGGC CGCACATGCT 1920

CGGGCCTCGC CTACGATTTC CAGCTCTGCA ACTCGCAGGA CTGCCCTGAC GCGCTGGCCG 1980

ACTTCCGCGA GGAGCAGTGC CGGCAGTGGG ACCTGTACTT CGAGCATGGT GACGCTCAAC 2040

ACCACTGGCT GCCCCACGAG CACCGGGACG CCAAGGAGCG GTGTCATCTC TACTGTGAGT 2100

CCAAGGAGAC CGGGGAGGTG GTGTCCATGA AGCGTATGGT GCATGACGGG ACACGCTGTT 2160

CCTACAAGGA CGCCTTCAGC CTCTGCGTGC GTGGGGACTG CAGGAAGGTG GGCTGTGACG 2220

GGGTGATCGG CTCCAGCAAG CAGGAGGACA AGTGTGGTGT GTGCGGAGGG GACAACTCCC 2280

ACTGCAAGGT GGTCAAGGGC ACGTTCTCGC GCTCGCCCAA GAAGCTTGGT TACATCAAGA 2340

TGTTTGAGAT CCCGGCAGGA GCCAGACACC TGCTAATCCA GGAAGCAGAC ACCACCAGCC 2400

ATCACCTGGC CGTCAAAAAC CTGGAGACAG GCAAGTTCAT TTTAAATGAG 2450

(2) INFORMATION FOR SEQ ID NO:10:

(i) SEQUENCE CHARACTERISTICS:
(A) LENGTH: 2130 base pairs
(B) TYPE: nucleic acid
(C) STRANDEDNESS: single
(D) TOPOLOGY: linear (xi) SEQUENCE DESCRIPTION: SEQ ID NO:10:

GAGAATGACG TGGATCCCAA CTCCAAGACC TTCATCGCCA TGGGCGTGGA GTGGGAGTAC 60

CGGGATGAGG ACGGCCGGGA GACGCTGCAG ACCATGGGCC CCCTCCACGG CACCATCACT 120

GTGCTGGTCA TCCCAGAGGG GGACGCCCGC ATCTCACTGA CCTACAAGTA CATGATCCAT 180

GAGGACTCGC TCAATGTGGA TGACAACAAC GTCCTGGAAG ACGACTCTGT GGGCTATGAG 240

TGGGCCCTGA AGAAGTGGTC GCCCTGCTCC AAGCCCTGCG GTGGAGGGTC CCAATTCACC 300

AAGTATGGCT GCCGCCGGAG GCTGGACCAC AAGATGGTGC ACCGAGGCTT CTGCGACTCC 360

GTCTCAAAGC CCAAAGCCAT CCGCCGGACC TGCAACCCAC AGGAGTGCTC CCAGCCCGTG 420

TGGGTCACGG GTGAGTGGGA GCCGTGCAGC CGGAGCTGTG GGCGGACAGG CATGCAGGTT 480

CGCTCTGTGC GCTGTGTTCA GCCTCTGCAC AACAACACCA CCCGCTCCGT GCACACCAAG 540

CACTGCAATG ACGCTCGACC CGAGGGCCGC CGGGCCTGCA ACCGCGAGCT GTGCCCTGGC 600

CGGTGGCGGG CTGGATCCTG GTCCCAGTGC TCAGTAACCT GTGGAAACGG CACCCAGGAA 660

CGGCCAGTGC TCTGCCGAAC TGCGGACGAC AGTTTCGGGG TGTGCCGGGA GGAGCGGCCT 720

GAGACGGCAA GGATCTGCAG GCTTGGCCCC TGTCCCCGAA ACACCTCTGA CCCCTCCAAG 780

AAGAGCTACG TGGTCCAGTG GCTATCCCGA CCGGACCCCA ACTCGCCAGT CCAGGAGACC 840

TCGTCAAAGG GCCGCTGCCA AGGTGACAAG TCAGTGTTCT GTAGGATGGA AGTCTTGTCT 900

CGTTATTGCT CCATCCCAGG CTACAATAAG CTGTGCTGCA AGTCCTGTAA CCCGCACGAC 960

AACCTCACTG ATGTGGACGA CAGGGCAGAG CCACCCTCTG GGAAGCACAA TGACATTGAA 1020

GAGCTCATGC CCACCCTTTC AGTGCCCACT CTAGTCATGG AGGTGCAGCC TCCGCCAGGC 1080

ATACCCCTGG AGGTGCCTCT CAATACTTCC AGCACCAATG CCACCGAGGA CCATCCAGAA 1140

ACCAATGCTG TGGATGTGCC CTACAAAATC CCTGGCCTGG AAGATGAAGT CCAGCCACCC 1200

```
AACCTGATCC CTCGACGACC GAGCCCATAT GAAAAGACCA GAAACCAAAG AATCCAAGAG  1260

CTCATTGATG AGATGAGGAA GAAAGAGATG CTCGGAAAGT TCTAATAAAA TGGAAAGATA  1320

GCATCAATAG CTTTTTTTTG CTTGCTTATA GAGATATTCC ATGGCAACTC CTGTGTTGTG  1380

GAGATGAAGT CAGATTCCTG ACTCCAAAAG GTTTTGAGGA AACAAAGAAG GAGAATAATG  1440

TAAATATATA GCTATATTTA CATTATACAC ACACACACAC ACACACATAG TTGTAAGCAT  1500

GTGGCAACTA GGTTGGTACC TATGTTTCCT AGTCCTGGAA TGTTCTAAGT CCTGCACTGG  1560

GGTTGGGTGT GGGGTAGAGA GGAATATGGA GGCTCTACAC CTCCCATCAA TGAGGGACAG  1620

CAGGAGGGAG AGAAAAAACC TTTGCCCCAA GTTTCTGAGC AGTGATTGCG AATCTTTTCC  1680

TTGCGGTGAC AACCCTGCTG GAGACGCAGG ACAGTTCCTA CCAATCTCCA GGTTGAGGTA  1740

CAAGACCCAT GGGGCTCTTA CAAGAAACAG TGATTTATTT ACTAAGTGAC CAGTCATTAA  1800

GACGAATGCA GTGAAGTGGA GGTCATGAAT TCCAGCAAAC TCCAGGACGA GGTGGTGAGG  1860

CAGGTGGCGT GGATGAGTGT GGTCACCAGC TGGCACTCCC AGGCTCTCAC ACCTCTCTCT  1920

TCTTCACTAA CCTTGGCCTT GCTTGTCACC TCTGGCCAGC CTGGCCTCAG GCCTGGGGCT  1980

CCCCAGAGAC ACTCTCTGCT TCCTCAAGTC ACTGGAAGGA TGAAGGAGGC ATGCACTCTG  2040

CTGGAAAATC CAGTGAGTGG TCAGGGCTCA TTTTTCTGTG TGTGAACATG TAGCTTAAAC  2100

TTCCCGAAAT TACAGGACCC AAACACCAAG                                    2130
```

(2) INFORMATION FOR SEQ ID NO:11:

(i) SEQUENCE CHARACTERISTICS:
(A) LENGTH: 1205 amino acids
(B) TYPE: amino acid
(C) STRANDEDNESS: single
(D) TOPOLOGY: linear (xi) SEQUENCE DESCRIPTION: SEQ ID NO:11:

```
Met Asp Pro Pro Ala Gly Ala Ala Gly Arg Leu Leu Cys Pro Ala Leu
 1               5                  10                  15

Leu Leu Leu Leu Leu Leu Pro Leu Pro Ala Asp Ala Arg Leu Ala Ala
            20                  25                  30

Ala Ala Ala Asp Pro Pro Gly Gly Pro Gln Gly His Gly Ala Glu Arg
        35                  40                  45

Ile Leu Ala Val Pro Val Arg Thr Asp Ala Gln Gly Arg Leu Val Ser
    50                  55                  60

His Val Val Ser Ala Ala Thr Ala Pro Ala Gly Val Arg Thr Arg Arg
65                  70                  75                  80

Ala Ala Pro Ala Gln Ile Pro Gly Leu Ser Gly Gly Ser Glu Glu Asp
                85                  90                  95

Pro Gly Gly Arg Leu Phe Tyr Asn Tyr Thr Val Phe Gly Arg Asp Leu
            100                 105                 110

His Leu Arg Leu Arg Phe Asn Ala Arg Leu Val Ala Pro Gly Ala Thr
        115                 120                 125

Val Glu Trp Gln Gly Glu Ser Gly Ala Thr Arg Val Glu Pro Leu Leu
    130                 135                 140

Gly Thr Cys Leu Tyr Val Gly Asp Val Ala Gly Leu Ala Glu Ser Ser
145                 150                 155                 160

Ser Val Ala Leu Ser Asn Cys Asp Gly Leu Ala Gly Leu Ile Arg Met
                165                 170                 175

Glu Glu Glu Glu Phe Phe Ile Glu Pro Leu Glu Lys Gly Leu Ala Ala
            180                 185                 190
```

-continued

```
Lys Glu Ala Glu Gln Gly Arg Val His Val Val Tyr His Arg Phe Thr
        195                 200                 205

Thr Ser Arg Phe Phe Phe Leu Gly Gly Phe Gln Ala Leu Asp Thr Gly
    210                 215                 220

Ile Ser Ala Asp Ser Leu Asp Ser Leu Ser Arg Ala Leu Gly Val Leu
225                 230                 235                 240

Glu Glu Arg Val Asn Ser Ser Arg Arg Arg Met Arg Arg His Ala Ala
                245                 250                 255

Asp Asp Asp Tyr Asn Ile Glu Val Leu Leu Gly Val Asp Asp Ser Val
            260                 265                 270

Val Gln Phe His Gly Thr Glu His Val Gln Lys Tyr Leu Leu Thr Leu
        275                 280                 285

Met Asn Ile Val Asn Glu Ile Tyr His Asp Glu Ser Leu Gly Ala His
    290                 295                 300

Ile Asn Val Val Leu Val Arg Ile Ile Leu Leu Ser Tyr Gly Lys Ser
305                 310                 315                 320

Met Ser Leu Ile Glu Ile Gly Asn Pro Ser Gln Ser Leu Glu Asn Val
                325                 330                 335

Cys Arg Trp Ala Tyr Leu Gln Gln Lys Pro Asp Thr Asp His Asp Glu
            340                 345                 350

Tyr His Asp His Ala Ile Phe Leu Thr Arg Gln Asp Phe Gly Pro Ser
        355                 360                 365

Gly Met Gln Gly Tyr Ala Pro Val Thr Gly Met Cys His Pro Val Arg
    370                 375                 380

Ser Cys Thr Leu Asn His Glu Asp Gly Phe Ser Ser Ala Phe Val Val
385                 390                 395                 400

Ala His Glu Thr Gly His Val Leu Gly Met Glu His Asp Gly Gln Gly
                405                 410                 415

Asn Arg Cys Gly Asp Glu Val Arg Leu Gly Ser Ile Met Ala Pro Leu
            420                 425                 430

Val Gln Ala Ala Phe His Arg Phe His Trp Ser Arg Cys Ser Gln Gln
        435                 440                 445

Glu Leu Ser Arg Tyr Leu His Ser Tyr Asp Cys Leu Arg Asp Asp Pro
    450                 455                 460

Phe Thr His Asp Trp Pro Ala Leu Pro Gln Leu Pro Gly Leu His Tyr
465                 470                 475                 480

Ser Met Asn Glu Gln Cys Arg Phe Asp Phe Gly Leu Gly Tyr Met Met
                485                 490                 495

Cys Thr Ala Phe Arg Thr Phe Asp Pro Cys Lys Gln Leu Trp Cys Ser
            500                 505                 510

His Pro Asp Asn Pro Tyr Phe Cys Lys Thr Lys Lys Gly Phe Pro Leu
        515                 520                 525

Asp Gly Thr Met Cys Ala Pro Gly Lys His Cys Phe Lys Gly His Cys
    530                 535                 540

Thr Trp Leu Thr Phe Asp Ile Leu Lys Arg Asp Gly Asn Trp Gly Ala
545                 550                 555                 560

Trp Ser Pro Phe Gly Ser Cys Ser Arg Thr Cys Gly Thr Gly Val Lys
                565                 570                 575

Phe Arg Thr Arg Gln Cys Asp Asn Pro His Pro Ala Asn Gly Gly Arg
            580                 585                 590

Thr Cys Ser Gly Leu Ala Tyr Asp Phe Gln Leu Cys Asn Ser Gln Asp
        595                 600                 605
```

-continued

```
Cys Pro Asp Ala Leu Ala Asp Phe Arg Glu Glu Gln Cys Arg Gln Trp
    610                 615                 620

Asp Leu Tyr Phe Glu His Gly Asp Ala Gln His His Trp Leu Pro His
625                 630                 635                 640

Glu His Arg Asp Ala Lys Glu Arg Cys His Leu Tyr Cys Glu Ser Lys
                645                 650                 655

Glu Thr Gly Glu Val Val Ser Met Lys Arg Met Val His Asp Gly Thr
            660                 665                 670

Arg Cys Ser Tyr Lys Asp Ala Phe Ser Leu Cys Val Arg Gly Asp Cys
        675                 680                 685

Arg Lys Val Gly Cys Asp Gly Val Ile Gly Ser Ser Lys Gln Glu Asp
    690                 695                 700

Lys Cys Gly Val Cys Gly Gly Asp Asn Ser His Cys Lys Val Val Lys
705                 710                 715                 720

Gly Thr Phe Ser Arg Ser Phe Lys Lys Leu Gly Tyr Ile Lys Met Phe
                725                 730                 735

Glu Ile Pro Ala Gly Ala Arg His Leu Leu Ile Gln Glu Ala Asp Thr
            740                 745                 750

Thr Ser His His Leu Ala Val Lys Asn Leu Glu Thr Gly Lys Phe Ile
        755                 760                 765

Leu Asn Glu Glu Asn Asp Val Asp Pro Asn Ser Lys Thr Phe Ile Ala
    770                 775                 780

Met Gly Val Glu Trp Glu Tyr Arg Asp Glu Asp Gly Arg Glu Thr Leu
785                 790                 795                 800

Gln Thr Met Gly Pro Leu His Gly Thr Thr Thr Val Leu Val Ile Pro
                805                 810                 815

Glu Gly Asp Ala Arg Ile Ser Leu Thr Tyr Lys Tyr Met Ile His Glu
            820                 825                 830

Asp Ser Leu Asn Val Asp Asp Asn Asn Val Leu Glu Asp Asp Ser Val
        835                 840                 845

Gly Tyr Glu Trp Ala Leu Lys Lys Trp Ser Pro Cys Ser Lys Pro Cys
    850                 855                 860

Gly Gly Gly Ser Gln Phe Thr Lys Tyr Gly Cys Arg Arg Arg Leu Asp
865                 870                 875                 880

His Lys Met Val His Arg Gly Phe Cys Asp Ser Val Ser Lys Pro Lys
                885                 890                 895

Ala Ile Arg Arg Thr Cys Asn Pro Gln Glu Cys Ser Gln Pro Val Trp
            900                 905                 910

Val Thr Gly Glu Trp Glu Phe Cys Ser Arg Ser Cys Gly Arg Thr Gly
        915                 920                 925

Met Gln Val Arg Ser Val Arg Cys Val Gln Pro Leu His Asn Asn Thr
    930                 935                 940

Thr Arg Ser Val His Thr Lys His Cys Asn Asp Ala Arg Pro Glu Gly
945                 950                 955                 960

Arg Arg Ala Cys Asn Arg Glu Leu Cys Pro Gly Arg Trp Arg Ala Gly
                965                 970                 975

Ser Trp Ser Gln Cys Ser Val Thr Cys Gly Asn Gly Thr Gln Glu Arg
            980                 985                 990

Phe Val Leu Cys Arg Thr Ala Asp Asp Ser Phe Gly Val Cys Arg Glu
        995                 1000                1005

Glu Arg Phe Glu Thr Ala Arg Ile Cys Arg Leu Gly Pro Cys Phe Arg
    1010                1015                1020

Asn Thr Ser Asp Pro Ser Lys Lys Ser Tyr Val Val Gln Trp Leu Ser
```

-continued

```
1025                1030                1035                104

Arg Pro Asp Pro Asn Ser Phe Val Gln Glu Thr Ser Ser Lys Gly Arg
                1045                1050                1055

Cys Gln Gly Asp Lys Ser Val Phe Cys Arg Met Glu Val Leu Ser Arg
            1060                1065                1070

Tyr Cys Ser Ile Pro Gly Tyr Asn Lys Leu Cys Cys Lys Ser Cys Asn
        1075                1080                1085

Pro His Asp Asn Leu Thr Asp Val Asp Asp Arg Ala Glu Pro Pro Ser
    1090                1095                1100

Gly Lys His Asn Asp Ile Glu Glu Leu Met Pro Thr Leu Ser Val Pro
1105                1110                1115                112

Thr Leu Val Met Glu Val Gln Pro Pro Pro Gly Ile Pro Leu Glu Val
                1125                1130                1135

Pro Leu Asn Thr Ser Ser Thr Asn Ala Thr Glu Asp His Pro Glu Thr
            1140                1145                1150

Asn Ala Val Asp Val Pro Tyr Lys Ile Pro Gly Leu Glu Asp Glu Val
        1155                1160                1165

Gln Pro Pro Asn Leu Ile Pro Arg Arg Pro Ser Pro Tyr Glu Lys Thr
    1170                1175                1180

Arg Asn Gln Arg Ile Gln Glu Leu Ile Asp Glu Met Arg Lys Lys Glu
1185                1190                1195                120

Met Leu Gly Lys Phe
                1205
```

(2) INFORMATION FOR SEQ ID NO:12:

(i) SEQUENCE CHARACTERISTICS:
(A) LENGTH: 12 amino acids
(B) TYPE: amino acid
(C) STRANDEDNESS: single
(D) TOPOLOGY: linear (ix) FEATURE:
(A) NAME/KEY: Other
(B) LOCATION: 4
(D) OTHER INFORMATION: Xaa = Phe or Val
(A) NAME/KEY: Other
(B) LOCATION: 7
(D) OTHER INFORMATION: Xaa = Phe or Gln or Val
(A) NAME/KEY: Other
(B) LOCATION: 8
(D) OTHER INFORMATION: Xaa = Asp or Tyr or Pro (xi) SEQUENCE DESCRIPTION: SEQ ID NO:12:

```
Asn Asp Asp Xaa Asn Leu Xaa Xaa Glu His Ile Met
 1               5                  10
```

(2) INFORMATION FOR SEQ ID NO:13:

(i) SEQUENCE CHARACTERISTICS:
(A) LENGTH: 35 base pairs
(B) TYPE: nucleic acid
(C) STRANDEDNESS: single
(D) TOPOLOGY: linear (ix) FEATURE:
(A) NAME/KEY: Other
(B) LOCATION: 20
(D) OTHER INFORMATION: N = Inosine
(A) NAME/KEY: Other
(B) LOCATION: 23
(D) OTHER INFORMATION: N = Inosine (xi) SEQUENCE DESCRIPTION: SEQ ID NO:13:

-continued

```
TTGTCATCMA MGTTCAGSWN RKNCTCATGG ATCAT                          35


(2) INFORMATION FOR SEQ ID NO:14:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ix) FEATURE:
          (A) NAME/KEY: Other
          (B) LOCATION: 10
          (D) OTHER INFORMATION: N = Inosine

          (xi) SEQUENCE DESCRIPTION: SEQ ID NO:14:

RTTRTCRTCN AMRTT                                                15


(2) INFORMATION FOR SEQ ID NO:15:

     (i) SEQUENCE CHARACTERISTICS:
          (A) LENGTH: 14 amino acids
          (B) TYPE: amino acid
          (C) STRANDEDNESS: single
          (D) TOPOLOGY: linear

          (xi) SEQUENCE DESCRIPTION: SEQ ID NO:15:

Lys Ser Asn Pro Asp Val Asp Asn Glu Glu Asn Leu Ile Phe
 1               5                  10


(2) INFORMATION FOR SEQ ID NO:16:

     (i) SEQUENCE CHARACTERISTICS:
          (A) LENGTH: 22 base pairs
          (B) TYPE: nucleic acid
          (C) STRANDEDNESS: single
          (D) TOPOLOGY: linear

    (ix) FEATURE:
          (A) NAME/KEY: Other
          (B) LOCATION: 5
          (D) OTHER INFORMATION: N = Inosine

          (xi) SEQUENCE DESCRIPTION: SEQ ID NO:16:

GRTCNACRTC RTTYTCYTCR TT                                        22


(2) INFORMATION FOR SEQ ID NO:17:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ix) FEATURE:
          (A) NAME/KEY: Other
          (B) LOCATION: 4
          (D) OTHER INFORMATION: N = Inosine

          (xi) SEQUENCE DESCRIPTION: SEQ ID NO:17:

YTTNSWRTTN GGRTC                                                15
```